(12) United States Patent
Ali et al.

(10) Patent No.: US 9,809,717 B2
(45) Date of Patent: *Nov. 7, 2017

(54) ANTIMICROBIAL-COATED MEDICAL ARTICLES

(75) Inventors: Mahfuza B. Ali, Mendota Heights, MN (US); Naiyong Jing, Woodbury, MN (US); Valeri Lirine, Brighton, MA (US); Pradnya V. Nagarkar, Weston, MA (US); Caroline M. Ylitalo, Stillwater, MN (US); Nancy S. Lennhoff, North Andover, MA (US); Matthew T. Scholz, Woodbury, MN (US); Ranjani V. Parthasarathy, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 228 days.

This patent is subject to a terminal disclaimer.

(21) Appl. No.: 13/699,345

(22) PCT Filed: May 25, 2011

(86) PCT No.: PCT/US2011/037966
§ 371 (c)(1),
(2), (4) Date: Jan. 15, 2013

(87) PCT Pub. No.: WO2011/150103
PCT Pub. Date: Dec. 1, 2011

(65) Prior Publication Data
US 2015/0024019 A1 Jan. 22, 2015

Related U.S. Application Data

(60) Provisional application No. 61/348,157, filed on May 25, 2010, provisional application No. 61/348,044, filed on May 25, 2010.

(51) Int. Cl.
| | | |
|---|---|---|
| *A61L 29/08* | (2006.01) |
| *C09D 5/16* | (2006.01) |
| *C03C 17/30* | (2006.01) |
| *C03C 17/42* | (2006.01) |
| *C08F 220/34* | (2006.01) |
| *C08G 77/26* | (2006.01) |
| *C09D 183/10* | (2006.01) |
| *G06F 3/041* | (2006.01) |
| *A61L 29/16* | (2006.01) |
| *B05D 3/02* | (2006.01) |
| *B05D 3/06* | (2006.01) |
| *G06F 3/047* | (2006.01) |
| *C08F 220/06* | (2006.01) |
| *C08F 220/18* | (2006.01) |
| *C08F 230/08* | (2006.01) |

(52) U.S. Cl.
CPC .......... *C09D 5/1637* (2013.01); *A61L 29/085* (2013.01); *A61L 29/16* (2013.01); *B05D 3/02* (2013.01); *B05D 3/06* (2013.01); *C03C 17/30* (2013.01); *C03C 17/42* (2013.01); *C08F 220/34* (2013.01); *C08G 77/26* (2013.01); *C09D 5/1675* (2013.01); *C09D 5/1693* (2013.01); *C09D 183/10* (2013.01); *G06F 3/041* (2013.01); *G06F 3/047* (2013.01); *A61L 2300/216* (2013.01); *A61L 2300/404* (2013.01); *A61L 2420/02* (2013.01); *C08F 220/06* (2013.01); *C08F 220/18* (2013.01); *C08F 230/08* (2013.01); *Y10T 428/31663* (2015.04)

(58) Field of Classification Search
None
See application file for complete search history.

(56) References Cited

U.S. PATENT DOCUMENTS

| | | |
|---|---|---|
| 3,250,808 A | 5/1966 | Moore |
| 4,052,524 A | 10/1977 | Harakas et al. |
| 4,259,103 A | 3/1981 | Malek |
| 4,682,992 A | 7/1987 | Fuchs |
| 4,968,116 A | 11/1990 | Hulme-Lowe |
| 5,013,459 A | 5/1991 | Gettings |
| 5,084,096 A | 1/1992 | Stovicek |
| 5,239,026 A | 8/1993 | Babirad |
| 5,266,222 A | 11/1993 | Willis |
| 5,408,022 A | 4/1995 | Imazato |
| 5,569,732 A | 10/1996 | Nohr |

(Continued)

FOREIGN PATENT DOCUMENTS

| | | |
|---|---|---|
| EP | 1 748 353 | 1/2007 |
| GB | 1 433 303 | 4/1976 |
| JP | H07-502053 | 3/1995 |
| JP | WO 1998/30615 | 7/1998 |
| JP | WO 2001/01957 | 1/2001 |
| JP | 2001-508480 | 6/2001 |
| JP | 2003-503157 | 1/2003 |
| JP | WO 2008/006912 | 1/2008 |
| JP | 2009-543895 | 12/2009 |
| KR | 2008-0025467 | 3/2008 |

(Continued)

OTHER PUBLICATIONS https://www.britannica.com/science/carboxylic-acid retrieved on Apr. 29, 2017.*

(Continued)

*Primary Examiner* — Jessica Worsham

(57) ABSTRACT

The disclosure provides polymers having antimicrobial activity and articles with the polymers coated thereon. The polymers include a first pendant group comprising a first cationic component, a second pendant group comprising a nonpolar component, and a third pendant group comprising an organosilane component. The disclosure also includes methods of coating medical device articles and body fluid-receiving substrates with the antimicrobial polymers. The methods further include the use of adhesion-promoting components.

18 Claims, No Drawings

(56) References Cited

U.S. PATENT DOCUMENTS

| | | |
|---|---|---|
| 5,907,015 A | 5/1999 | Sexsmith |
| 6,015,597 A | 1/2000 | David |
| 6,238,798 B1 | 5/2001 | Kang |
| 6,406,758 B1 | 6/2002 | Bottari et al. |
| 6,504,582 B1 | 1/2003 | Li |
| 6,504,583 B2 | 1/2003 | Li |
| 6,587,097 B1 | 7/2003 | Aufderheide et al. |
| 6,696,157 B1 | 2/2004 | David |
| 6,795,636 B1 | 9/2004 | Cronk |
| 6,852,781 B2 | 2/2005 | Savu |
| 7,157,649 B2 | 1/2007 | Hill |
| 7,179,773 B2 | 2/2007 | Cannon |
| 7,291,386 B2 | 11/2007 | Richter |
| 7,294,405 B2 | 11/2007 | Richter |
| 7,342,080 B2 | 3/2008 | Qiu |
| 7,459,167 B1 | 12/2008 | Sengupta |
| 2001/0013907 A1 | 8/2001 | Li |
| 2004/0077775 A1 | 4/2004 | Audenaert et al. |
| 2004/0233174 A1 | 11/2004 | Robrecht |
| 2005/0008763 A1* | 1/2005 | Schachter .............. 427/2.24 |
| 2005/0124724 A1 | 6/2005 | Burton |
| 2005/0134574 A1 | 6/2005 | Hill |
| 2005/0147655 A1 | 7/2005 | Bagwell et al. |
| 2005/0249940 A1 | 11/2005 | Klun |
| 2005/0259378 A1 | 11/2005 | Hill |
| 2006/0046078 A1 | 3/2006 | Ricther |
| 2006/0188537 A1 | 8/2006 | Lamba-Kohli |
| 2007/0160781 A1 | 7/2007 | Landon |
| 2007/0163964 A1 | 7/2007 | Williamson |
| 2008/0014340 A1 | 1/2008 | Richter et al. |
| 2008/0064825 A1 | 3/2008 | Jing |
| 2008/0196664 A1 | 8/2008 | David |
| 2009/0130157 A1 | 5/2009 | Ylitalo et al. |
| 2009/0252647 A1 | 10/2009 | Orofino |
| 2011/0008403 A1 | 1/2011 | Nakamura et al. |
| 2011/0163992 A1 | 7/2011 | Cordeiro |

FOREIGN PATENT DOCUMENTS

| | | |
|---|---|---|
| WO | WO 1993/01221 | 1/1993 |
| WO | WO 2002-092336 | 11/2002 |
| WO | WO 2003-093906 | 11/2003 |
| WO | WO 2004-087226 | 10/2004 |
| WO | WO 2005-095285 | 10/2005 |
| WO | WO 2005-113641 | 12/2005 |
| WO | WO 2005-113642 | 12/2005 |
| WO | WO 2006/025992 | 3/2006 |
| WO | WO 2006-121937 | 11/2006 |
| WO | WO 2007/056856 | 5/2007 |
| WO | WO 2007-070650 | 6/2007 |
| WO | WO 2008-042631 | 4/2008 |
| WO | WO 2008-157323 | 12/2008 |
| WO | WO 2009-030640 | 3/2009 |
| WO | WO 2009-030641 | 3/2009 |
| WO | WO 2009-037430 | 3/2009 |
| WO | WO 2009/113438 | 9/2009 |
| WO | WO 2009-137188 | 11/2009 |
| WO | WO 2010-036465 | 4/2010 |
| WO | WO 2010-048436 | 4/2010 |
| WO | WO 2011/084917 | 7/2011 |

OTHER PUBLICATIONS

Isquith, A.J. et al.; "Surface-Bonded Antimicrobial Activity of an Organosilicon Quaternary Ammonium Chloride"; Applied Microbiology; vol. 24, No. 6; 1972; pp. 859-863.

Brochure entitled "Material Safety Data Sheet 3M 906 Abrasion Resistant Coating" dated Feb. 16, 2011 (9 pgs).

* cited by examiner

ANTIMICROBIAL-COATED MEDICAL ARTICLES

CROSS REFERENCE TO RELATED APPLICATIONS

This application is the National Stage filing under 35 U.S.C. 371 of International Application No. PCT/US2011/037966, , filed May 25, 2011, which claims the benefit of U.S. Provisional Patent Application Nos. 61/348,044 and 61/348,157, both filed on May 25, 2010, , which each is incorporated herein by reference in its entirety.

BACKGROUND

Surfaces that are intended to be touched by human operators or contacted with human tissue, accordingly, will be exposed to the microorganisms either typically or incidentally found on skin and mucosal tissue. Of particular concern are surfaces that will be in contact with tissue for extended periods of time where bacteria can colonize, grow, and potentially form a biofilm. These surfaces are notorious for causing infection. For example, venous access catheters, urinary catheters, endotracheal tubes, nasal gastric tubes, feeding tubes and other devices which enter a natural or created orifice are at risk for causing infections which can have very serious consequences for the patient. Biofilms are structured communities of microorganisms encased in an extracellular polymeric matrix that typically are tenaciously adhered to the surface of biomaterials and host tissue. Bacterial biofilms are a significant issue in the development of materials that are exposed to aqueous and body fluids for prolonged periods for several different application areas: medical devices, filtration systems for food processing and other industrial applications, coatings for marine structures and other anti-fouling applications. Bacteria living in a biofilm are considerably more resistant to host defenses and antibiotic or antimicrobial treatments, when compared to "free" pathogens, and thereby increase the potential for infections during the use of in-dwelling and other tissue contacting devices.

Biofilms are believed to have a significant role in catheter associated urinary tract infections (CAUTI) and ventilator associated pneumonia (VAP). CAUTIs comprise the largest percentage of hospital acquired infections (HAIs) and are the second most common cause of nosocomial bloodstream infections. VAP has the highest morbidity of all HAIs, as roughly 15% of patients with VAP will die. VAP may also be the most expensive HAI to treat ($20,000-$50,000 per episode), and has an incident rate between 25% and 40% for patients having longer term urinary catheters.

By way of example, and without wishing to be bound by theory, biofilm formation on urinary catheter surfaces may proceed as follows: 1) The catheter surface is initially colonized by bacteria (some of them urease-producing bacteria) originally present on the periurethral skin and able to migrate into the bladder between the epithelial surface of the urethra and the catheter once the catheter is inserted. The adsorption of these cells to the catheter surface may be facilitated by the formation of an organic conditioning film made up largely of adsorbed proteins. 2) A bacterial biofilm community forms, encased primarily by a matrix of bacterial exopolysaccharide. The pioneer biofilm forming bacteria that initially cause urinary tract infections (UTIs) are typically *S. epidermidis*, *E. coli* or *E. faecalis*, with *E. coli* the overwhelming cause of CAUTI. At longer catheterization times, other species appear including *P. aeruginosa*, *P. mirabilis*, and *K. pneumoniae*. These latter stage bacteria are more difficult to treat with antibiotics while the catheter is in place. 3) The presence of a growing biofilm, including bacterial species that are capable of producing urease, leads to an elevation of the urine's pH due to the action of urease on urea. 4) As the urine becomes alkaline, calcium phosphate and magnesium ammonium phosphate crystals precipitate and accumulate in the biofilm matrix growing on the catheter surface. 5) Continued crystal formation in the alkaline urine and continued growth of the biofilm lead to severe encrustation and eventually blockage of the device which necessitates re-catherization of the patient. Thus, preventing colonization and biofilm formation on the catheter could play a large role preventing CAUTIs as well as blood stream infections (BSIs).

Attempts have been made to provide surfaces that are inherently antimicrobial, either by composition or use of antimicrobial drug delivery systems. These surfaces can be insufficiently effective in reducing biofilm formation for three important reasons: 1) when used as a delivery system, antimicrobial or active agents may be exhausted well before the end of the service lifetime of the medical article; 2) the surface antimicrobial properties are eventually impaired as dead cells, the high organic load in the urethra, and other adsorbed biomaterial mask the antimicrobial properties of that surface; and 3) antimicrobial agents in the catheter material or in an external coating fail to elute sufficiently.

Thus surfaces of certain medical devices and particularly those that are in contact with moist mammalian tissue provide a suitable home for bacteria, fungi, algae, and other single celled microrganisms which thrive and propagate based on the availability of appropriate amounts of moisture, temperature, nutrients, and receptive surfaces. As these organisms metabolize, they produce chemical by-products. These chemicals can be toxins and/or pyrogens. Thus, these microorganisms, as well as their metabolic products can pose serious health risks to users ranging from minor tissue irritation to more serious toxic response and disease.

Further complicating the matter is that most venous access catheters, urinary catheters, endotracheal tubes, NG tubes and other patient contact devices are made from flexible and often elastomeric plastics. Furthermore, these devices can be moved and flexed repeatedly during insertion and use. It can be exceedingly difficult to adhere to such surfaces.

There exists a need for simple means to prevent the colonization of articles by microorganisms and/or a means to reduce the number of living microorganisms that become disposed on a surface in a manner that will durably adhere to flexible and elastomeric substrates.

SUMMARY

In view of the general need to control the number of viable microorganisms on a surface that is intentionally contacted with mammalian skin or muscosal tissue or internal tissues, the present disclosure provides an antimicrobial polymer composition that can be used, in some embodiments, to form a coating that is bonded to a flexible and/or elastomeric surface. The antimicrobial polymer may include chemical components that impart other desirable properties (e.g., antiadhesive properties, lubriciousness or lower coefficient of friction to facilitate insertion, increase in surface energy, and the like.) for the article on which it is applied. These cationic silanes preferable impart or improve the antimicrobial activity of the adhered substantially nonleachable composition. In some embodiments, the components of the polymer may be selected for their optically-transparent properties.

Thus, in one aspect, the present disclosure provides an article. The article can comprise a coating composition comprising a vinyl polymer having a plurality of pendant groups, and a medical device comprising an elastomeric first substrate having a patient-contact first surface and a second surface. The pendant groups can comprise a first pendant group comprising a cationic component, a second pendant group comprising a nonpolar component, and a third pendant group comprising a first organosilicon component. The vinyl polymer can be durably adhered to the patient-contact first surface. The coating composition can be essentially free of inorganic filler.

In any of the above embodiments of the article, the cationic component can be selected from the group consisting of a quaternary amine component, protonated tertiary amine component, and a protonated secondary amine component. In any of the above embodiments, the organosilicon component comprises an organosilane or an organic silane ester.

In any of the above embodiments, the coating composition can be deposited and cured with an additional free silane present in the coating composition. In some embodiments, the additional free silane can be a quarternary ammonium silane or protonated tertiary amino silane having at least one straight or branched chain alkyl of 6-22 carbon atoms. In any of the above embodiments, the coating composition further can comprise an adhesion-promoting component.

In some embodiments, the polymer may not comprise a pendant group that includes a carboxylate or alkoxylate chemical group.

In any of the above embodiments, in the vinyl polymer, the ratio of cationic amine molar equivalents to organosilicon molar equivalents can be about 0.1:1 to about 10:1. In any of the above embodiments, the total nonleachable cationic amine concentration derived from cationic groups on the polymer and any cationic quaternary amino, protonated tertiary amino, or protonated secondary amino silane present can be at least 300 grams nonvolatile coating composition/equivalent cationic group and not more than 3000 grams nonvolatile coating composition/equivalent cationic group. In any of the above embodiments, the silane equivalent weight of the coating composition derived from silane functionality on the polymer and on any free silane present in the coating composition can be at least 200 grams of nonvolatile coating composition/equivalent silane and not more than 4000 grams nonvolatile coating composition/equivalent silane group.

In any of the above embodiments, at least one of the pendant components can comprise a fluorochemical. In some embodiments, the second pendant group can comprise a fluorochemical.

In any of the above embodiments, the patient-contact surface to which the organic polymer is adhered can be a glass, metal, metal oxide, ceramic, or polymeric surface. In any of the above embodiments, the first substrate further can comprise a durable metal oxide layer on the first surface.

In any of the above embodiments, the second side of the first substrate can be adhered to a second substrate. In some embodiments, the first substrate can be adhered to the second substrate by a chemical bond, a thermal bond, an adhesive, a mechanical fastener, or a combination of any of the foregoing. In any of the above embodiments, the medical device comprises an endoscope, an endotracheal tube, an intravascular catheter, a urinary catheter, a wound dressing, a stethoscope diaphragm, stethoscope tubing, ventilator tubing, patient feeding tubes, surgical drains, and other flat, tubular or shaped flexible medical devices intended for contact with mammalian tissue.

In another aspect, the present disclosure provides an article. The article can comprise a coating composition comprising a vinyl polymer having a plurality of pendant groups, and a medical device comprising an elastomeric first substrate having a body fluid-contacting first surface and a second surface. The pendant groups can comprise a first pendant group comprising a cationic component, a second pendant group comprising a nonpolar component, and a third pendant group comprising a first organosilicon component. The vinyl polymer can be durably adhered to the body fluid-contacting first surface. The coating composition can be essentially free of inorganic filler.

In any of the above embodiments of the article, the cationic component can be selected from the group consisting of a quaternary amine component, protonated tertiary amine component, and a protonated secondary amine component. In any of the above embodiments, the organosilicon component comprises an organosilane or an organic silane ester.

In any of the above embodiments, the coating composition can be deposited and cured with an additional free silane present in the coating composition. In some embodiments, the additional free silane can be a quarternary ammonium silane or protonated tertiary amino silane having at least one straight or branched chain alkyl of 6-22 carbon atoms. In any of the above embodiments, the coating composition further can comprise an adhesion-promoting component.

In some embodiments, the polymer may not comprise a pendant group that includes a carboxylate or alkoxylate chemical group.

In any of the above embodiments, in the vinyl polymer, the ratio of cationic amine molar equivalents to organosilicon molar equivalents can be about 0.1:1 to about 10:1. In any of the above embodiments, the total nonleachable cationic amine concentration derived from cationic groups on the polymer and any cationic quaternary amino, protonated tertiary amino, or protonated secondary amino silane present can be at least 300 grams nonvolatile coating composition/equivalent cationic group and not more than 3000 grams nonvolatile coating composition/equivalent cationic group. In any of the above embodiments, the silane equivalent weight of the coating composition derived from silane functionality on the polymer and on any free silane present in the coating composition can be at least 200 grams of nonvolatile coating composition/equivalent silane and not more than 4000 grams nonvolatile coating composition/equivalent silane group.

In any of the above embodiments, at least one of the pendant components can comprise a fluorochemical. In some embodiments, the second pendant group can comprise a fluorochemical.

In any of the above embodiments, the body fluid-contacting surface to which the organic polymer is adhered can be a glass, metal, metal oxide, ceramic, or polymeric surface. In any of the above embodiments, the first substrate further can comprise a durable metal oxide layer on the first surface.

In any of the above embodiments, the second side of the first substrate can be adhered to a second substrate. In some embodiments, the first substrate can be adhered to the second substrate by a chemical bond, a thermal bond, an adhesive, a mechanical fastener, or a combination of any of the foregoing.

In yet another aspect, the present disclosure provides a method of making a coated article. The method can comprise forming a coating composition comprising a vinyl polymer having a plurality of pendant groups and contacting the coating composition with a first surface of a first substrate under conditions suitable to adhere the polymer to the first surface. The plurality of pendant groups can comprise a first pendant group comprising a first cationic component, a second pendant group comprising a nonpolar component, and a third pendant group comprising a first organosilicon component. The composition can be essentially free of inorganic filler. The first substrate can comprise an elastomeric component of a medical device. In any embodiment of the method, forming a first coating composition can comprise forming an emulsion or a dispersion of the vinyl polymer in a solvent. In any of the above embodiments of the method, the vinyl polymer further can comprise a third pendant group, wherein the third pendant group comprises a nonpolar component. In any of the above embodiments of the method, forming the first coating composition further can comprise forming a first coating composition comprising a catalyst compound to accelerate the silane hydrolysis and/or condensation reactions during cure. In any of the above embodiments of the method, forming the first coating composition further can comprise forming a first coating composition comprising an adhesion promoter. In any of the above embodiments of the method, forming a first coating composition further can comprise forming a first coating composition comprising a free second cationic silane component and/or a second cationic component. In any of the above embodiments, the method further can comprise after contacting the first coating composition with the surface, rinsing the surface. In any of the above embodiments, the method further can comprise coupling the first substrate to a second substrate. In any of the above embodiments, the method further can comprise contacting a second coating composition with the first surface of the first substrate prior to contacting the first coating composition with the first surface of the first substrate. In yet another aspect, the present disclosure provides an article made according to any of the above embodiments of the method.

In yet another aspect, the present disclosure provides a method of making a coated article. The method can comprise forming a coating composition comprising a vinyl polymer having a plurality of pendant groups and contacting the coating composition with a first surface of a first substrate under conditions suitable to adhere the polymer to the first surface. The plurality of pendant groups can comprise a first pendant group comprising a first cationic component, a second pendant group comprising a nonpolar component, and a third pendant group comprising a first organosilicon component. The composition can be essentially free of inorganic filler. The first substrate can comprise an elastomeric body fluid-contacting substrate. In any embodiment of the method, forming a first coating composition can comprise forming an emulsion or a dispersion of the vinyl polymer in a solvent. In any embodiment of the method, the vinyl polymer further can comprise a third pendant group, wherein the third pendant group comprises a nonpolar component. In any embodiment of the method, forming the first coating composition further can comprise forming a first coating composition comprising a catalyst compound to accelerate the silane hydrolysis and/or condensation reactions during cure. In any embodiment of the method, forming the first coating composition further can comprise forming a first coating composition comprising an adhesion promoter. In any embodiment of the method, forming a first coating composition further can comprise forming a first coating composition comprising a free second cationic silane component and/or a second cationic component. In any embodiment, the method further can comprise after contacting the first coating composition with the surface, rinsing the surface. In any embodiment, the method further can comprise coupling the first substrate to a second substrate. In any embodiment, the method further can comprise contacting a second coating composition with the first surface of the first substrate prior to contacting the first coating composition with the first surface of the first substrate. In yet another aspect, the present disclosure provides an article made according to any embodiment of the method.

In yet another aspect, the present disclosure provides a medical device article comprising a coating. The coating can be derived from a composition comprising a free silane component and a vinyl polymer having a plurality of pendant groups. The pendant groups can comprise a first pendant group comprising a first quaternary ammonium component and a second pendant group comprising a first organosilicon component. The vinyl polymer can be durably adhered to the surface. In any embodiment, the composition can be essentially free of inorganic filler. In any embodiment, the free silane can be a quaternary ammonium silane. In any embodiment, the free quaternary ammonium silane can comprise at least one linear or branched C8-C22 alkyl group attached to the quaternary amine.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, an article comprising "a" siliceous substrate can be interpreted to mean that the article can include "one or more" siliceous substrates.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

Polymeric materials are provided that can contain a plurality of different pendant groups. As used herein a "pendant group" refers to a group that is not part of the main backbone chain of the polymer. Methods of making the polymeric material and compositions that contain the polymeric material are also provided. Additionally, articles with coatings that contain the polymeric material are provided. The polymeric material in the coatings is often crosslinked. The coatings can be antimicrobial, nonleachable, durably antimicrobial, durably adherent even to flexible and elastomeric substrates, water insoluble, abrasion resistant, or any combination thereof.

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways. Also, it is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The term "patient-contact surface" refers a surface of a medical device that is intended to contact mammalian skin, tissue, body fluids, naturally-occurring or created body orifices (e.g., intravenous access orifice, surgical orifice) or a body cavity.

The term "antimicrobial" refers to material that kills microorganisms or inhibits their growth.

The term "cationic" or "cationic group" refers to amine groups having a positive charge such as quaternary amine groups, protonated tertiary amine groups and protonated secondary amine groups. It is understood that these groups would be associated with a negatively charged counterion which may be any suitable counterion having one or more negative charges. Typical counterions include halides, organic carboxylates, sulfates, and phosphates including alpha- and beta-hydroxyacids, sulfate, methosulfate, alkylsulfate, phosphate, etc.

The term "silane" refers to a compound having four groups attached to a silicon atom. That is, the silane has a silicon-containing group.

The term "alkoxysilyl" refers to a silicon-containing group having an alkoxy group bonded directly to the silicon atom. The alkoxysilyl can be, for example, of formula —Si(OR)(Rx)$_2$ where R is an alkyl and each Rx is independently a hydroxyl, alkoxy, alkyl, perfluoroalkyl, aryl, aralkyl, or part of a silicone.

The term "ester equivalent" means groups such as silane amides (RNR'Si), silane alkanoates (RC(O)OSi), Si—O—Si, SiN(R)—Si, SiSR and RCONR'Si that are thermally and/or catalytically displaceable by R"OH. R and R' are independently chosen and can include hydrogen, alkyl, arylalkyl, alkenyl, alkynyl, cycloalkyl, and substituted analogs such as alkoxyalkyl, aminoalkyl, and alkylaminoalkyl. R" may be the same as R and R' except it may not be H.

The term "hydroxysilyl" refers to a silicon-containing group having a hydroxyl group bonded directly to the silicon atom. The hydroxysilyl can be, for example, of formula —Si(OH)(Rx)$_2$ where Rx is an alkyl, perfluoralkyl, aryl, aralkyl, alkoxy, hydroxyl, or part of a silicone. A compound having a hydroxysilyl group is often referred to as a "silanol". Silanols are a subset of silanes.

The term "silicone" or "siloxane" refers to a moiety that contains a silicon-oxygen-silicon linkage group. Any other suitable groups can be attached to the silicon atoms. Such a linkage can result from the reaction of a first silane (e.g., a first silicon-containing group such as a first alkoxysilyl group or hydroxysilyl group) with a second silane (e.g., a second silicon-containing group such as a second alkoxysilyl group or hydroxysilyl group). In some embodiments, the silicone is part of a "silicone network". A silicone network results when a first silane (i.e., a first silicon-containing group) reacts with a second silane (e.g., a second silicon-containing group) plus a third silane (e.g., a third silicon-containing group such as a third alkoxysilyl group or hydroxysilyl group) or when a first silane (e.g., a first silicon-containing group) reacts with a second silane (e.g., a second silicon-containing group) plus a third silane (e.g., a third silicon-containing group) and a fourth silane (e.g., a fourth silicon-containing group such as a fourth alkoxysilyl group or hydroxysilyl group).

As used herein, the phrases "polymeric material with a plurality of pendant groups", "polymeric material with multiple pendant groups", or similar phrases are used interchangeably to refer to a polymeric material that has at least three different types of pendant groups. The multiple pendant groups include (1) a first pendant group containing a cationic group; (2) a second pendant group containing a nonpolar group; and (3) a third pendant group having an organosilane group. The polymeric material with multiple pendant groups can be crosslinked through a condensation reaction of multiple organosilane groups. Furthermore, the polymeric material can be covalently coupled to a surface comprising a metal hydroxide group such as a silanol group or, preferably, a plurality of silanol groups.

As used herein, the term "body fluid-contacting substrate" refers to any surface that may come into contact one or more times with mammalian body fluids including but not limited to blood, urine, feces, saliva, wound exudate, spinal fluid, and the like. Examples include disposable medical devices such as catheters as well as durable surfaces such as patient thermometers, high touch surfaces in patient rooms such as bed rails, call buttons, door knobs, walls, curtains, trays, supply carts, intravenous pumps, lead wires, surgical lights, sinks, medical equipment used in an operating room or intensive care unit, and the like.

As used herein the term "non-leaching" means that the antimicrobial composition does not substantially diffuse out of or away from the polymer-coated composition while in contact with an aqueous liquid, as measured by the Antimicrobial Leaching Test Procedure described hereinbelow.

As used herein, "free silane" refers to a silane compound that does not comprise a vinyl group and, therefore, it is incapable of reacting with the vinyl polymer backbone. The free silane is, however, capable of reacting with silane pendant groups on the vinyl polymer. In some embodiments, "free silanes" may have antimicrobial properties. Exemplary antimicrobial free silanes can be found, in U.S. Pat. No. 5,013,459 (column 7, line 30 through column 9, line 9), which is incorporated herein by reference in its entirety.

The present disclosure is generally directed to medical devices comprising an antimicrobial coating and methods of making said devices comprising an antimicrobial coating. Many of the devices further comprise a patient-contact surface. In some embodiments, the substrate comprises a flexible or elastomeric substrate.

As used herein flexible refers to materials that can be easily bent 90 degrees by hand. Typically these can be bent easily by hand 180 degrees back upon itself three or more times in a row without visible damage to the material.

As used herein "elastomer" or "elastomeric" refers to materials that can reversibly extend at least 25%. Preferred elastomers are those that can reversibly extend at least 50%. When stretched to these extents the elastomers recover almost full (e.g. 95%) of the original length in less than 30 seconds.

Antimicrobial Polymers:

The present disclosure provides antimicrobial polymers. The antimicrobial polymers are formed by reacting, in suitable aqueous or organic solvent, monomers that comprise a chemical group that serves one or more functional purposes in the polymer.

In some embodiments, the antimicrobial polymers can be coated (e.g., as a film or layer) onto a substrate as described herein. The polymers have antimicrobial activity that can kill or inhibit microorganisms that come into contact with the polymer (e.g., on the surface of a touch panel). The antimicrobial activity can be tested using a standardized antimicrobial resistance test such as, for example, JIS-Z 2801 (Japanese Industrial Standards; Japanese Standards Association; Tokyo, Japan). In some embodiments, the polymers further can have abrasion-resistant properties. The abrasion-resistant property of the polymer, when coated on a relatively hard surface, can be tested using the ASTM test method D 7027.26676.

Polymers of the present disclosure are formed in any suitable solvent (e.g., an organic solvent) that will solublize or make a dispersion of the resultant polymer. Suitable organic solvents have a boiling point about 200° C. or lower and can be mixed with small portions (<10%, w/w) of acidified water without substantially degrading the solvent properties. Adding the acidified water to the solvent facilitates complete hydrolysis of silane groups which, in turn optimizes the formation of —Si—O—Si— bonds within the polymer and between the polymer and the substrate. This can result in improved durability of antimicrobial coating on the substrate. Preferably, the solvent flashpoint is 100° C. or lower. Nonlimiting examples of suitable organic solvents include an alcohol (e.g., isopropyl alcohol, methanol), MEK, acetone, DMF, DMAC (dimethyl acetamide,) ethyl acetate, THF, etc. The monomers are mixed with the solvent and reacted to form an antimicrobial polymer. Suitable monomers include derivatives of acrylate monomers, methacrylate monomers, vinyl monomers, and olefinic monomers. The monomers comprise chemical groups that are pendant from the polymer backbone after the polymerization reaction. The pendant groups include a first cationic group, an optional nonpolar group, and a first organosilane group (e.g., trimethoxysilylpropane).

The polymer shown in Structure (I) shows a representation of a portion of an antimicrobial polymer made from acrylate or olefinic monomers according to the present disclosure.

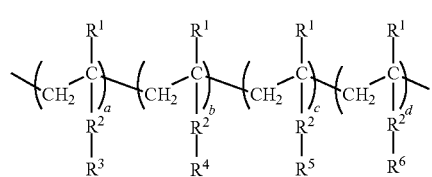

(I)

Polymers of the present disclosure include pendant groups with antimicrobial activity. The groups with antimicrobial activity can be selected for properties that are desirable in the articles on which the polymer is coated. For example, the antimicrobial group can be selected because it provides a polymer having substantial optical clarity (i.e. high optical transmission throughout a narrow or broad spectrum of wavelengths, low haze) or a low coefficient of friction. These properties easily can be measured by a person of ordinary skill in the art, for example, by methods disclosed herein. In the exemplary polymer of Structure (I), the first cationic pendant group includes the cationic moiety $R^3$ and can be derived from a monomer where: $R^1$=H or $CH_3$, $R^2$=COO, CO, $C_1$-$C_{12}$ alkyl, aryl $R^3$=a cationic having the formula

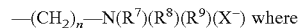

$—(CH_2)_n—N(R^7)(R^8)(R^9)(X^−)$ where n=1-3 (i.e., an alkyl group from $C_1$-$C_3$,)

$R^7$, $R^8$, and $R^9$ are independently an alkyl ($C_1$-$C_{22}$), aryl, or a combination of chemical groups forming a ring structure and up to 2 of $R^7$, $R^8$, and $R^9$ may be H; and

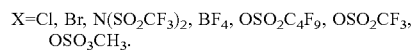

X=Cl, Br, $N(SO_2CF_3)_2$, $BF_4$, $OSO_2C_4F_9$, $OSO_2CF_3$, $OSO_3CH_3$.

$R^3$ also may be selected from other antimicrobial quaternary ammonium groups as disclosed in U.S. Pat. No. 5,408,022 which is incorporated herein by reference.

The first cationic pendant groups are coupled (e.g., covalently coupled) to the polymer such that, the bactericidal activity of the antimicrobial coupled to the polymer is insoluble in water (i.e., the antimicrobial is non-leaching when the polymer is contacted with an aqueous composition). Suitable antimicrobial cationic compounds include any protonated secondary amine, protonated tertiary amine, or quaternary amine having at least one $C_6$-$C_{22}$ linear or branched chain alkyl or alkenyl group. Quaternary amine groups in compositions of the present disclosure can include quaternary amine groups that are pendant groups in the polymer, as well as free quaternary amine groups, as described herein.

Nonlimiting examples of suitable antimicrobial cationic components on the polymer and/or antimicrobial silane include the hexadecyldimethylethylamine, octadecyldimethylethylamine, hexadecyldimethylpropylamine, hexadecydimethylamine hydrochloride, lauryldimethylamine hydrobromide, and octadecyldimethylpropylamine.

In the exemplary polymer of Structure (I), the nonpolar pendant group includes the nonpolar moiety $R^4$ and can be derived from a monomer where $R^4$ is an unsubstituted or substituted alkyl group ($C_4$ to $C_{22}$), an aryl group, perfluoroalkyl sulfonamide, perfluoroalkyl sulfone, perfluoroalkyl carboxamide, a class of free-radically reactive fluoroalkyl or fluoroalkylene group-containing compatibilizers of the respective chemical formulas: $R_{ff}Q_3(X_1)_{n1}$ and $(X_1)_{n1}Q_3R_{ff2}Q_3(X_1)_{n1}$), where $R_{ff}$ is a fluoroalkyl, $R_{ff2}$ is a fluoroalkylene, $Q_3$ is a connecting group of valency at least 2 and is selected from the group consisting of a covalent bond, an alkylene, an arylene, an aralkylene, an alkarylene group, a straight or branched chain or cycle-containing connecting group optionally containing heteroatoms such as O, N, and S and optionally a heteroatom-containing functional group such as carbonyl or sulfonyl, and combinations thereof; $X_1$ is a free-radically reactive group selected from (meth)acryl, —SH, allyl, or vinyl groups and n1 is independently 1 to 3. Typical $Q_3$ groups include: —$SO_2N(R)CH_2CH_2$—; —$SO_2N(CH_2CH_2)_2$—; —$(CH_2)_m$—; —$CH_2O(CH_2)_3$—; and —C(O)NRCH$_2$CH$_2$—, where R is H or lower alkyl of 1 to 4 carbon atoms and m is 1 to 6. Preferably the fluoroalkyl or fluoroalkylene group is a perfluoroalkyl or perfluoroalkylene group. Exemplary, non-limiting perfluorobutyl-substituted acrylate compatibilizers meeting these criteria and useful in the present invention include one or more of C$_4$F$_9$SO$_2$N(CH$_3$)CH$_2$CH$_2$OC(O)CH═CH$_2$, C$_4$F$_9$SO$_2$N(CH$_2$CH$_2$OC(O)CH═CH$_2$)$_2$, or C$_4$F$_9$SO$_2$N(CH$_3$)CH$_2$CH$_2$OC(O)C(CH$_3$)═CH$_2$. One non-limiting example of a preferred fluoroalkyl-substituted monomers that may be utilized in the composition of the coat layer is: (1H,1H,2H,2H)-perfluorodecyl acrylate, available from Lancaster Synthesis of Windham, New Hampshire. Numerous other (meth)acryl compounds with perfluoroalkyl moieties that may also be utilized in the composition of the coat layer are mentioned in U.S. Pat. No. 4,968,116, to Hulme-Lowe et al., and in U.S. Pat. No. 5,239,026 (including perfluorocyclohexylmethyl methacrylate), to Babirad et al., and are herein incorporated by reference. Other fluorochemical (meth)acrylates that meet these criteria and may be utilized include, for example, 2,2,3,3,4,4,5,5-octafluorohexanediol diacrylate and ω-hydro 2,2,3,3,4,4,5,5-octafluoropentyl acrylate (H—C$_4$F$_8$—CH$_2$O—C(O)—CH═CH$_2$). Other fluorochemical (meth)acrylates that may be used alone, or as mixtures, are described in U.S. Pat. No. 6,238,798, to Kang et al., and herein incorporated by reference.

Another monomer that may be used is a fluoroalkyl- or fluoroalkylene-substituted thiol or polythiol. Non-limiting examples of this type of monomers includes one or more of the following: C$_4$F$_9$SO$_2$N(CH$_3$)CH$_2$CH$_2$OC(O)CH$_2$SH, C$_4$F$_9$SO$_2$N(CH$_3$)CH$_2$CH$_2$OC(O)CH$_2$CH$_2$SH, C$_4$F$_9$SO$_2$N(CH$_3$)CH$_2$CH$_2$SH, and C$_4$F$_9$SO$_2$N(CH$_3$)CH(OC(O)CH$_2$SH)CH$_2$OC(O)CH$_2$SH.

In another preferred embodiment, the coating composition adds one or more multi-olefinic compounds bearing at least one monovalent poly(hexafluoropropylene oxide) (HFPO) moiety and optionally a compatibilizer such as a fluoroalkyl- or fluoroalkylene-substituted mono or multi-acrylate such as C$_4$F$_9$SO$_2$N(CH$_3$)CH$_2$CH$_2$OC(O)CH═CH$_2$, C$_4$F$_9$SO$_2$N(CH$_2$CH$_2$OC(O)CH═CH$_2$)$_2$, or C$_4$F$_9$SO$_2$N(CH$_3$)CH$_2$CH$_2$OC(O)C(CH$_3$)═CH$_2$, alcohol, olefin, thiol or polythiol to fluoropolymer curing composition. Non-limiting examples of thiol or polythiol type of compatibilizer includes one or more of the following: C$_4$F$_9$SO$_2$N(CH$_3$)CH$_2$CH$_2$OC(O)CH$_2$SH, C$_4$F$_9$SO$_2$N(CH$_3$)CH$_2$CH$_2$OC(O)CH$_2$CH$_2$SH, C$_4$F$_9$SO$_2$N(CH$_3$)CH$_2$CH$_2$SH, and C$_4$F$_9$SO$_2$N(CH$_3$)CH(OC(O)CH$_2$SH)CH$_2$OC(O)CH$_2$SH.

As used in the examples, unless otherwise noted, "HFPO-" refers to the end group F(CF(CF$_3$)CF$_2$O)$_a$CF(CF$_3$)- of the methyl ester F(CF(CF$_3$)CF$_2$O)$_a$CF(CF$_3$)C(O)OCH$_3$, wherein "a" averages about 6.8, and the methyl ester has an average molecular weight of 1,211 g/mol, and which can be prepared according to the method reported in U.S. Pat. No. 3,250,808 (Moore et al.), the disclosure of which is incorporated herein by reference, with purification by fractional distillation.

The mono- or multi-olefinic compound bearing at least one monovalent poly(hexafluoropropylene oxide) (HFPO) moiety preferably is in the form of a multiacrylate. These materials are of the formula: R$_{fpe}$Q(X)$_n$ wherein Rfpe is the residue of a monovalent HFPO moiety, Q is a connecting group comprising an alkylene, arylene, arylene-alkylene, or alkylene-arylene group and may comprise a straight or branched chain connecting group which may contain heteroatoms such as O, N, and S, X is a free-radically reactive group selected from meth(acryl), allyl, or vinyl groups and n is 2 to 3. Typical Q group include: —(CH$_2$)$_m$—; —CH$_2$O(CH$_2$)$_3$—; and —C(O)NRCH$_2$CH$_2$—, where R is H or lower alkyl of 1 to 4 carbon atoms and m is 1 to 6.

One class of multi-(meth)acryl compound bearing at least one monovalent poly(hexafluoropropylene oxide) (HFPO) moiety comprises compounds described in U.S. Provisional Application No. 60/569,351 entitled "Fluoropolyether Polyacryl Compounds", filed May 7, 2004, the disclosure of which is incorporated by reference.

Other mono- and multi-(meth)acryl compounds bearing at least one monovalent poly(hexafluoropropylene oxide) (HFPO) moiety comprise compounds which are Michael adducts of HFPO amine derivatives with multiacrylates described in U.S. application Ser. No. 10/841,792, entitled "Polymerizable Compositions, Methods Of Making The Same, And Composite Articles Therefrom," filed May 7, 2004, the disclosure of which is incorporated by reference.

The optional nonpolar pendant group is a chemical group that increases the relative hydrophobicity of the antimicrobial polymer. The nonpolar pendant groups are selected for their ability to influence the surface energy of the polymer. In particular, the nonpolar pendant groups are selected to impart a low surface energy polymer. Nonpolar pendant groups can also increase the scratch resistance of the polymer, when the polymer is coated onto a hard surface (e.g., glass). Nonlimiting example of suitable nonpolar groups include linear or branched alkanes (e.g., isooctane, isobutane), alkaryl, aralkyl, and aromatic groups.

In the exemplary polymer of Structure (I), the first organosilane pendant group includes the siloxane moiety R$^5$ and can be derived from a monomer where:
R$^5$═(CH$_2$)m—Si(OR$^{10}$)$_3$,
m=1-6 (i.e., an alkyl group from C$_1$-C$_6$,) and
R$^{10}$═an alkyl group from C$_1$-C$_3$.

The first organosilane pendant group includes a silicon-containing group. This pendant group can crosslink the antimicrobial polymeric material, bond the antimicrobial polymeric material to a substrate, bond a second organosilane to the antimicrobial polymer, or it can confer the ability of the polymer to perform any combination of the foregoing bonding configurations. A nonlimiting example of a suitable organosilane pendant group is the propyl trimethoxysilane group found in methacryloylpropyl trimethoxysilane.

Although Structure (I) shows a portion of an exemplary antimicrobial polymer comprising three sequential monomers with different pendant groups, it will be recognized that the antimicrobial polymer of the present disclosure is a random copolymer, with the number and order of monomeric subunits (a, b, c, and, optionally, d) influenced by the respective ratios of monomeric units in the polymerization reaction and/or the polymerization reaction conditions.

Antimicrobial polymers of the present disclosure optionally can include, in addition to the cationic, nonpolar, and organosilane pendant groups, a fourth pendant group that includes a polar component. The polar pendant group can confer adhesive properties that allow the antimicrobial polymer to adhere to certain substrates. Because the polar pendant groups promote adhesion of the antimicrobial polymer to the substrate, advantageously, this can result in an improved durability of the polymer on the substrate. In some embodiments, the polar pendant group may enhance the antimicrobial activity of the polymer. Suitable polar pendant groups include, for example, N-hydroxymethylacrylamide, dimethylacrylamide, and alcohol groups.

In some embodiments, the antimicrobial polymer of the present disclosure does not comprise a pendant group that includes a carboxylate or alkoxylate chemical group.

Antimicrobial polymers of the present disclosure can be synthesized by reacting, in an organic solvent, monomers comprising the pendant groups. Suitable monomers for the reaction include, for example, acrylate monomers, methacrylate monomers, acylamide and methacrylamide monomers and combinations thereof. Other suitable monomers for the reaction include vinyl monomers and olefinic monomers.

The monomers can be combined, on a weight percent basis, in various ratios in the reaction. In some embodiments, the monomer comprising the cationic pendant group can comprise from about 20% to about 80% of the monomers reacted to form a polymer. In some embodiments, the monomer comprising the cationic pendant group can comprise greater than 20% of the monomers reacted to form a polymer. In some embodiments, the monomer comprising the cationic pendant group can comprise greater than 30% of the monomers reacted to form a polymer. In some embodiments, the monomer comprising the cationic pendant group can comprise greater than 40% of the monomers reacted to form a polymer. In some embodiments, the monomer comprising the cationic pendant group can comprise greater than 50% of the monomers reacted to form a polymer. In some embodiments, the monomer comprising the cationic pendant group can comprise greater than 60% of the monomers reacted to form a polymer. In some embodiments, the monomer comprising the cationic pendant group can comprise greater than 70% of the monomers reacted to form a polymer. In some embodiments, the monomer comprising the cationic pendant group can comprise 70% to 80% of the monomers reacted to form a polymer. While it is possible that some cationic monomers may be reacted in an uncharged state the weight % calculation is based on the cationic form. For example, a tertiary amine acrylate may be reacted as a tertiary amine and subsequently protonated with an acid.

In some embodiments, the monomer comprising the nonpolar pendant group can comprise from about 20% to about 60% of the monomers reacted to form a polymer. In some embodiments, the monomer comprising the nonpolar pendant group can comprise greater than 20% of the monomers reacted to form a polymer. In some embodiments, the monomer comprising the nonpolar pendant group can comprise greater than 30% of the monomers reacted to form a polymer. In some embodiments, the monomer comprising the nonpolar pendant group can comprise 30% to 40% of the monomers reacted to form a polymer.

In some embodiments, the monomer comprising the organosilane pendant group can comprise from about 1% to about 20% of the monomers reacted to form a polymer. In some embodiments, the monomer comprising the organosilane pendant group can comprise greater than 2% of the monomers reacted to form a polymer. In some embodiments, the monomer comprising the organosilane pendant group can comprise greater than 5% of the monomers reacted to form a polymer. In some embodiments, the monomer comprising the organosilane pendant group can comprise greater than 10% of the monomers reacted to form a polymer. In some embodiments, the monomer comprising the organosilane pendant group can comprise greater than 15% of the monomers reacted to form a polymer. In some embodiments, the monomer comprising the organosilane pendant group can comprise 15% to 20% of the monomers reacted to form a polymer.

In some embodiments, the reaction mixture used to make the antimicrobial polymer comprises at least 20% monomers comprising a cationic pendant group, at least 20% monomers comprising a nonpolar pendant group, and at least 2% monomers comprising an organosilane pendant group.

The monomers are mixed in an organic solvent and are reacted under conditions suitable to form a polymer. For example, the reaction mixture can be purged with nitrogen to remove other dissolved gasses. In some embodiments, the reaction mixture can be sealed, heated, and mixed (e.g., mixed at 65° C.) for a period of time sufficient to allow polymerization of, for example, at least 99.5% of the monomers. In some embodiments, an additional initiator (e.g., 2,2-Azobis(2-methylbutyronitrile), available from DuPont of Wilmington, Del., USA, under the trade name Vazo-67) can be added to the mixture to react with any unreacted monomers from the original mixture. The extent of the reaction of monomers can be determined by, for example, a calculation of the percent solids in the mixture. The antimicrobial polymer typically comprises about 25 weight percent (wt %) of the composition in which it is made.

Antimicrobial Free Silane Components:

In certain preferred embodiments of this invention the coating composition also comprises a free antimicrobial silane component which is capable of reacting with itself and/or the organosilane component of the polymer during the coating and curing process. Suitable antimicrobial amines and quaternary ammonium salt silanes are disclosed in U.S. Pat. Nos. 5,408,022; 5,569,732; and 5,013,459; each of which is incorporated herein by reference in its entirety.

The silanes can have the general formula:

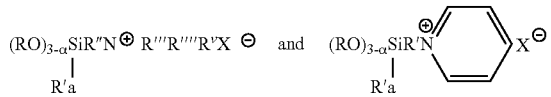

It should be noted that generically, these materials are quaternary ammonium salts of silanes. Most of the silanes falling within the scope of this invention are known silanes and references disclosing such silanes are numerous. One such reference; U.S. Pat. No. 4,259,103, which is incorporated herein by reference in its entirety; discusses the use of such silanes to render the surfaces of certain substrates antimicrobial. British Patent No. 1,433,303, which is incorporated herein by reference in its entirety shows the use of fillers treated with certain silanes to be used in paints and the like to give antimicrobial effects. Numerous publications have disclosed such silanes, for example, A. J. Isquith, E. A. Abbott and P. A. Walters, *Applied Microbiology, Vol.* 24, No. 6, December, 1972, pages 859-863.

For purposes of this invention, the silanes can be used neat or they can be used in solvent or aqueous-solvent solutions. When the silanes are used neat, the inventive process is preferably carried out in a system in which some small amount of water is present. If it is not possible to have a system with some small amount of water present, then a water soluble or water-dispersable, low molecular weight hydrolyzate of the silane may be used. What is important is the fact that the durability of any effect produced by the silane as part of a product requires that the silane molecule react with a surface to a certain extent. The most reactive species, as far as the silanes are concerned, is the ≡SiOH that is formed by hydrolysis of the alkoxy groups present on the silane. The ≡SiOH groups tend to react with the surface and bind the silanes to the surface.

Preferred for this invention is a reactive surface containing some small amount of water. By "reactive", it is meant that the surface must contain some groups which will react with some of the silanols generated by hydrolysis of the silanes of this invention.

R in the silanes of this invention are alkyl groups of 1 to 4 carbon atoms. Thus, useful as R in this invention are the methyl, ethyl, propyl and butyl radicals. In the above formulas RO can also be R. R can also be hydrogen thus indicating the silanol form, i.e. the hydrolyzate. The value of a is 0, 1 or 2 and R' is a methyl or ethyl radical. Because of the presence of these alkyl radicals, the prior art teaches that the materials must be stabilized with a corresponding solvent. Thus, methoxy groups require methanol and ethoxy groups require ethanol, for example.

R" for purposes of this invention is an alkylene group of 1 to 4 carbon atoms. Thus, R" can be alkylene groups such as methylene, ethylene, propylene, and butylene. R''', R'''', and $R^v$ are each independently selected from a group which consists of alkyl radicals of 1 to 18 carbons, $-CH_2C_6H_5$, $-CH_2CH_2OH$, $-CH_2OH$, and $-(CH_2)_xNHC(O)R^{vi}$, x has a value of from 2 to 10 and $R^{vi}$ is a perfluoroalkyl radical having from 1 to 12 carbon atoms. X is chloride, bromide, fluoride, iodide, acetate or tosylate.

Preferred for this invention are the silanes of the general formula:

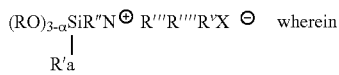

R is methyl or ethyl; a has a value of zero; R" is propylene; R''' is methyl or ethyl; R'''' and Rv are selected from alkyl groups containing 1 to 18 carbon atoms wherein at least one such group is larger than eight carbon atoms and x is either chloride, acetate or tosylate. Specific silanes within the scope of the invention are represented by the formulae:

$(CH_3O)_3Si(CH_2)_3N^+(CH_3)_2C_{18}H_{37}Cl^-$, $(CH_3O)_3Si(CH_2)_3N^+(CH_3)_2C_{18}H_{37}Br^-$, $(CH_3O)_3Si(CH_2)_3N^+(C_{10}H_{21})_2CH_3Cl^-$, $(CH_3O)_3Si(CH_2)_3N^+(C_{10}H_{21})_2CH_3Br^-$, $(CH_3O)_3Si(CH_2)_3N^+(CH_3)_2C_{18}H_{37}Cl^-$, $(CH_3O)_3SiCH_2CH_2CH_2P^+(C_6H_5)_3Cl^-$, $(CH_3O)_3SiCH_2CH_2CH_2P^+(C_6H_5)_3Br^-$, $(CH_3O)_3SiCH_2CH_2CH_2P^+(CH_3)_3Cl^-$, $(CH_3O)_3SiCH_2CH_2CH_2P^+(C_6H_{13})_3Cl^-$, $(CH_3)_3Si(CH_2)_3N^+(CH_3)_2C_{12}H_{25}Cl^-$, $(CH_3)_3Si(CH_2)_3N^+(C_{10}H_{21})_2CH_3Cl^-$, $(CH_3)_3Si(CH_2)_3N^+(CH_3)_2C_{18}H_{37}Cl^-$, $(CH_3O)_3Si(CH_2)_3N^+(CH_3)_2C_4H_9Cl^-$, $(C_2H_5O)_3Si(CH_2)_3N^+(CH_3)_2C_{18}H_{37}Cl^-$, $(CH_3O)_3Si(CH_2)_3N^+(CH_3)_2CH_2C_6H_5Cl^-$, $(CH_3O)_3Si(CH_2)_3N^+(CH_3)_2CH_2CH_2OHCl^-$,

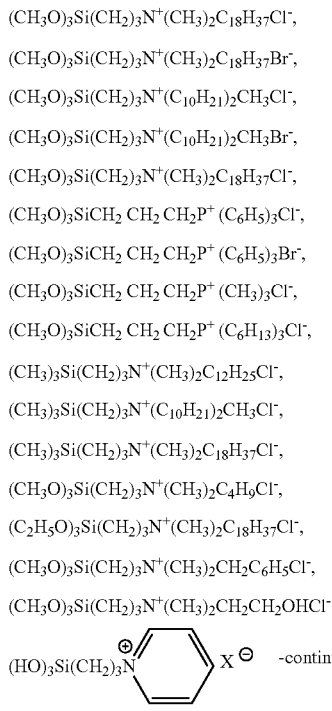

$(CH_3O)_3Si(CH_2)_3N^+(CH_3)_2(CH_2)_3NHC(O)(CF_3)_6CF_3Cl^-$, $(CH_3O)_3Si(CH_2)_3N^+(C_2H_5)_3Cl^-$.

Suitable protonated tertiary amines are described in U.S. Pat. No. 5,408,022.

Suitable protonated secondary amines include, but are not limited to, $C_6$-$C_{18}$ aminopropylmethacrylamide, $C_6$-$C_{18}$ aminoethylmethacrylate and the like.

Adhesion-Promoting Components:

In any embodiment the method of making an antimicrobial coating according the present disclosure, one or more adhesion-promoting component can be used in the process. Suitable adhesion-promoting components include organosilane compounds having a silane group that can react to form Si—O—Si linkages and a leaving group (e.g. an alkoxy group).

The adhesion-promoting component can form Si—O—Si linkages with another organosilane compound (e.g., an unreacted organosilane compound of the present disclosure), an organosilane-containing polymer (e.g., the antimicrobial polymers of the present disclosure), and/or a siliceous substrate (e.g., a polysiloxane). The adhesion promoting component also potentially can react with other metal oxide surfaces such as AlOx. Advantageously, the adhesion-promoting components promote improved adhesion of the antimicrobial coatings by increasing the number of attachment points (to the substrate) per antimicrobial molecule. Furthermore, the adhesion-promoting components promote improved durability of the antimicrobial coatings by increasing the number of intramolecular linkages per antimicrobial polymer molecule and/or the number of linkages between the antimicrobial polymer and the substrate.

In addition to promoting the formation of Si—O—Si bonds between the organosilane compounds in the coating compositions of the present disclosure, the preferred adhesion-promoting components can also be used as an adhesion promoter to increase the interfacial adhesion between the substrate and the antimicrobial polymer composition of the present disclosure.

Nonlimiting examples of suitable adhesion-promoting components include aminosilanes such as N-2(aminoethyl)-3-aminopropylmethyldimethoxysilane, N-2-(aminoethyl)-3-aminopropyltrimethoxysilane, N-2-(aminoethyl)-3-aminopropyltriethoxysilane, 3-aminopropyltrimethoxysilane, 3-aminopropyltriethoxysilane, 3-triethoxysilyl-N-(1,3-dimethyl-butyliden)propylamine, and N-phenyl-3-aminopropyltrimethoxysilane.

Mercaptosilanes such as 3-mercaptopropyltrialkoxysilanes can be used as well. In view of the present disclosure, other suitable adhesion-promoting components will be apparent to a person having ordinary skill in the art.

Other suitable adhesion-promoting components are disclosed in U.S. Patent Publication No. US 2008/0064825, which is incorporated herein by reference in its entirety. For example, amino-substituted organosilane esters (e.g., alkoxy silanes) are preferred adhesion-promoting components. The antimicrobial articles of the present disclosure may be made by reacting an amino-substituted organosilane ester or ester equivalent and an antimicrobial polymer that has a plurality of polar functionalities combinatively reactive with the silane ester or ester equivalent. The amino-substituted organosilane ester or ester equivalent bears on the silicon atom at least one ester or ester equivalent group, preferably 2, or more preferably 3 groups. Ester equivalents are well known to those skilled in the art and include compounds such as silane amides (RNR'Si), silane alkanoates (RC(O)OSi), Si—O—Si, SiN(R)—Si, SiSR and RCONR'Si. These ester equivalents may also be cyclic such as those derived from ethylene glycol, ethanolamine, ethylenediamine and their amides. R and R' are defined as in the "ester equivalent" definition herein.

3-aminopropyl alkoxysilanes are well known to cyclize on heating and these RNHSi compounds would be useful in this invention. Preferably, the amino-substituted organosilane ester or ester equivalent has ester groups such as methoxy that are easily volatilized as methanol so as to avoid leaving residue at the interface which may interfere with bonding The amino-substituted organosilane must have at least one ester equivalent; for example, it may be a trialkoxysilane.

For example, the amino-substituted organosilane may have the formula: ZNH-L-SiX'X"X"", where Z is hydrogen, alkyl, or substituted alkyl including amino-substituted alkyl; where L is a divalent straight chain C1-12 alkylene or may comprise a C3-8 cycloalkylene, 3-8 membered ring heterocycloalkylene, C2-12 alkenylene, C4-8 cycloalkenylene, 3-8 membered ring heterocycloalkenylene or heteroarylene unit. L may be interrupted by one or more divalent aromatic groups or heteroatomic groups. The aromatic group may include a heteroaromatic. The heteroatom is preferably nitrogen, sulfur or oxygen. L is optionally substituted with C1-4 alkyl, C2-4 alkenyl, C2-4 alkynyl, C1-4 alkoxy, amino, C3-6 cycloalkyl, 3-6 membered heterocycloalkyl, monocyclic aryl, 5-6 membered ring heteroaryl, C1-4 alkylcarbonyloxy, C1-4 alkyloxycarbonyl, C1-4 alkylcarbonyl, formyl, C1-4 alkylcarbonylamino, or C1-4 aminocarbonyl. L is further optionally interrupted by —O—, —S—, —N(Rc)—, —N(Rc)—C(O)—, —N(Rc)— —C(O)—O—, —O—C(O)—N(Rc)—, —N(Rc)—C(O)—N(Rd)—, —O—C(O)—, —C(O)—O—, or —O—C(O)—O—. Each of Rc and Rd, independently, is hydrogen, alkyl, alkenyl, alkynyl, alkoxyalkyl, aminoalkyl (primary, secondary or tertiary), or haloalkyl; and each of X', X" and X'" is a C1-18 alkyl, halogen, C1-8 alkoxy, C1-8 alkylcarbonyloxy, or amino group, with the proviso that at least one of X', X", and X"" is a labile group. Further, any two or all of X', X" and X'" may be joined through a covalent bond. The amino group may be an alkylamino group. Examples of amino-substituted organosilanes include 3-triethoxysilyl-N-(1,3-dimethyl-butyliden)propylamine, N-phenyl-3-aminopropyltrimethoxysilane, and 3-[2-(2-aminoethylamino)ethylamino] propyl-trimethoxysilane, 3-aminopropyltrimethoxysilane (SILQUEST A-1110), 3-aminopropyltriethoxysilane (SILQUEST A-1100), 3-(2-aminoethyl)aminopropyltrimethoxysilane (SILQUEST A-1120), SILQUEST A-1130, (aminoethylaminomethyl)phenethyltrimethoxysilane, (aminoethylaminomethyl) phenethyltriethoxysilane, N-(2-aminoethyl)-3-aminopropylmethyldimethoxysilane (SILQUEST A-2120), bis-(γ-triethoxysilylpropyl) amine (SILQUEST A-1170), N-(2-aminoethyl)-3-aminopropyltributoxysilane, 6-(aminohexylaminopropyl)trimethoxysilane, 4-aminobutyltrimethoxysilane, 4-aminobutyltriethoxysilane, p-(2-aminoethyl) phenyltrimethoxysilane, 3-aminopropyltris(methoxyethoxyethoxy)silane, 3-aminopropylmethyldiethoxysilane, tetraethoxysilane and oligomers thereof, methyltriethoxysilane and oligomers thereof, oligomeric aminosilanes such as DYNASYLAN 1146, 3-(N-methylamino)propyltrimethoxysilane, N-(2-aminoethyl)-3-aminopropylmethyldimethoxysilane, N-(2-aminoethyl)-3-aminopropylmethyldiethoxysilane, N-(2-aminoethyl)-3-aminopropyltrimethoxysilane, N-(2-aminoethyl)-3-aminopropyltriethoxysilane, 3-aminopropylmethyldiethoxysilane, 3-aminopropylmethyldimethoxysilane, 3-aminopropyldimethylmethoxysilane, and 3-aminopropyldimethylethoxysilane.

Additional "precursor" compounds such as a bis-silyl urea [RO]$_3$Si(CH$_2$)NR]$_2$C═O are also examples of amino-substituted organosilane ester or ester equivalent that liberate amine by first dissociating thermally. The amount of aminosilane is between 0.01% and 10% by weight relative to the functional polymer, preferably between 0.03% and 3%, and more preferably between 0.1% and 1%.

In some embodiments, the adhesion-promoting components can be added to a coating mixture comprising a first organosilane and a liquid crystal silane, as disclosed herein, and contacted with a substrate (e.g., a polysiloxane substrate) under conditions that facilitate the formation of Si—O—Si linkages, as described herein. The coating mixture can be contacted with a suitable substrate, as described herein. Accordingly, the silane group in the adhesion-promoting component can link a first organosilane molecule to another first organosilane molecule (which may optionally be a component of a polymeric structure), a cationic organosilane (e.g., the liquid crystal silane disclosed in U.S. Pat. No. 6,504,582, which is incorporated herein by reference in its entirety) molecule (which may optionally be a component of a polymeric structure); or the substrate; or the silane group in the adhesion-promoting component can link a liquid crystal silane molecule to another liquid crystal silane molecule (which may optionally be a component of a polymeric structure) or to the substrate.

In some embodiments, the adhesion-promoting components can be added to a coating mixture comprising a polymer having a plurality of pendant groups that include a first pendant group that includes a first cationic component, a second pendant group that includes a nonpolar component, and subsequently a third pendant group that includes an organosilane or organic silane ester component. Optionally, the coating mixture further can comprise a first organosilane, as described herein. The coating mixture can be contacted with a suitable substrate and heated as described herein to facilitate the formation of Si—O—Si bonds.

In an alternative embodiment, one or more adhesion-promoting component can be dissolved in an organic solvent and coated onto a suitable substrate (e.g., a polysiloxane substrate) as described herein to form a first coating. After removal of the solvent by evaporation, the substrate comprises a layer (i.e., a "primer layer" or "adhesion-promoting" layer) of the adhesion-promoting component coated thereon. Subsequently, a composition comprising any antimicrobial polymer of the present disclosure in organic solvent can be coated onto the primer layer. After removal of the solvent by evaporation, the substrate now comprises two layers, the "primer layer" and the antimicrobial polymer layer. The substrate, now comprising two coated layers, can be heated (e.g., to about 120 degrees C. for about 3 minutes to about 15 minutes) to facilitate the formation of Si—O—Si bonds and, thereby, covalently couple the polymer to the substrate.

Catalysts:

In any embodiment the method of making an antimicrobial coating according the present disclosure, one or more catalyst can be used in the process. Suitable catalysts include any compound that promotes the formation of Si—O—Si bonds. Nonlimiting examples of suitable catalysts include an acid (e.g., a mineral or an organic acid), a base (e.g., an organic base), tin octoate and 1,8-Diazabicycloundecene (DBU). In any embodiment, the catalyst can be added with the antimicrobial component and the adhesion-promoting component, if present, to the first coating composition described herein.

In use, the catalyst can be dissolved in the first coating composition, second coating composition, first mixture and/or second mixture described herein. Typically, the final concentration of the catalyst in any coating composition is relatively low (e.g., about 0.04 weight percent). A person of ordinary skill in the art will recognize that the concentration of the catalyst should be sufficiently high enough to catalyze the cross-linking reaction, while avoiding substantial interference with the optical properties (e.g., color) of the coating, if undesirable, and/or avoiding interference with the shelf-life of the coating mixture.

Substrates and Articles:

Antimicrobial polymers of the present disclosure can be applied as a coating to a variety of substrates. Useful substrates include, for example, flexible and/or elastomeric articles that may comprise and/or be coated with a layer comprising non-siliceous ceramic materials (e.g., carbides, borides, nitrides), siliceous materials such as glasses and siliceous ceramic materials (e.g., silicides), metals (e.g., stainless steel, titanium, gold, silver, chromium, cobalt, tantulum as well as alloys of these metals and alloys of these metals with other metals such as, for example, cobalt-chromium alloys and titanium alloys used in orthopedic implants), and/or metal oxides. The substrate may be films, sheets, tubes, fibers, and the like formed of polymeric materials that are either thermoplastic polymers or thermoset polymers. Exemplary polymeric substrates include, but are not limited to, thermoplastic and thermoset polymers that are optionally plactisized and include polyolefins, polyethylene, polypropylene, fluoropolymers, polyamides, polyethers, epoxies, polyvinyl chloride and plasticized polyvinylchloride, polyisoprene, polyisobutylene, block copolymers such as styrene-butadene styrene and styrene-isoprene styrene, hydrogenated versions of these available from Kraton Polymers, metallocene polyolefins, rayon polyester, polyethylene terephthalate (PET), poly(meth)acrylates, polycarbonates, polystyrenes, polystyrene copolymers such as styrene acrylonitrile copolymers, polyesters, polyethersulfone, acrylics and acrylic copolymers, polyacrylamides, and polyurethanes, silicones such as two part cured polydiemthylsiloxanes, natural rubber latex, polyisoprene, nitrile rubber, and the like, as well as combinations thereof including blends thereof and laminates thereof. Suitable degradeable polymer substrates include, for example, polylactic acid (PLA), polyglycolic acid (PGA), and combinations thereof.

The substrates can be used to fabricate a variety of useful articles (e.g., as a part, a portion, or the entirety of the article). The surface of the substrate may comprise one or more of a variety of surface topographies including, for example, substantially planar surfaces, contoured surfaces, microreplicated structures, and a combination of any two or more of the foregoing. The articles (e.g., medical devices) comprise a variety of surfaces that may be deliberately or incidentally contacted with microbiologically-contaminated items during routine use. Suitable articles may be found in health care environments (e.g., patient care rooms, countertops, bedrails, patient care equipment such as instruments and stethoscopes (including, for example, stethoscope diaphragms and/or tubing), and in-dwelling medical devices such as venous access catheters, nasal gastric tubes, shunts, myringotomy tubes, intrauterine devices, urinary catheters, patient feeding tubes, ventilator tubing, endotracheal tubes, and other flat, tubular, or shaped flexible medical devices intended for contact with mammalian tissue). Other nonlimiting exemplary medical devices that can be coated with an antimicrobial composition according to the present disclosure include contact lenses, intraocular lenses, artificial corneas, wound dressings, eye bandages, materials for the sustained release of an active compound such as a drug delivery patch, moldings that can be used in surgery, such as heart valves, vascular grafts, catheters, artificial organs, orthopedic implants, encapsulated biologic implants, e.g. pancreatic islets, materials for prostheses such as bone substitutes, or moldings for diagnostics, membranes or biomedical instruments or apparatus Methods of Preparing Antimicrobial Coated Articles:

The present disclosure provides methods for coating the antimicrobial polymer of the present disclosure onto a substrate. The composition (e.g., the reaction mixture) comprising the antimicrobial polymer in solvent (e.g., an aqueous solvent, an organic solvent) can be contacted with a substrate. The solvent can be evaporated to leave the antimicrobial polymer in the form of a coating on the substrate. In some embodiments, the substrate can be heated before and/or during the contacting step to accelerate the evaporation of the solvent. Preferably, the substrate is heated to a temperature that does not degrade the function of the polymer or a component of the substrate onto which the polymer is coated. A suitable temperature for contacting the polymer composition on a glass substrate is from room temperature to about 120° C. A person of ordinary skill in the art will recognize that higher temperatures will facilitate faster removal of organic solvent from the polymer composition.

In some embodiments, the antimicrobial polymer can be diluted to a final concentration of 1 wt. % to about 20 wt % in a solvent such as an organic solvent before using the diluted composition to coat the antimicrobial polymer onto a substrate. In some embodiments, the antimicrobial polymer is diluted to a final concentration of 1 wt % to about 5 wt % in the organic solvent before using the diluted composition to coat the antimicrobial polymer onto a substrate. Suitable organic solvents to dilute the polymer have a flashpoint below 150° C. and include ethers, ketones esters and alcohols, for example, isopropyl alcohol.

In any embodiment, in order to have sufficient antimicrobial activity the total nonleachable cationic amine concentration derived from cationic groups on the polymer and any cationic quaternary, protonated tertiary amino, or protonated secondary amino silane present is at least 300 grams nonvolatile coating composition/equivalent cationic group and not more than 3000 grams nonvolatile coating composition/equivalent cationic group, more preferably, less than 2000 grams of nonvolatile coating composition/equivalent cationic group, even more preferably, less than 1500 grams of nonvolatile coating composition/equivalent cationic group, even more preferably, less than 1000 grams of nonvolatile coating composition/equivalent cationic group. In some embodiments, the total nonleachable cationic amine concentration derived from cationic groups on the polymer and any cationic quaternary, protonated tertiary amino, or protonated secondary amino silane present is at least about 575 grams nonvolatile coating composition/equivalent cationic group to about 925 grams nonvolatile coating composition/equivalent cationic group. These compositions advantageously provide sufficient antimicrobial activity.

In order to provide sufficient adhesion and water insolubility (non-leaching) properties the silane equivalent weight of the coating composition derived from silane functionality on the polymer and on any free silane present in the coating composition is at least 200 grams (preferably, at least 300 grams) of nonvolatile coating composition/equivalent silane and not more than 4000 grams of nonvolatile coating composition/equivalent silane group. In some embodiments, the silane equivalent weight of the coating composition derived from silane functionality on the polymer and on any free silane present in the coating composition is at least about 143 grams to about 2484 grams of nonvolatile coating composition/equivalent silane. These compositions advantageously facilitate sufficient crosslinking of the polymer which provides adhesion of the composition to the substrate, durability of the coating on the substrate, and resistance to leaching.

In one embodiment, the method of preparing an antimicrobial polymer-coated surface includes the step of forming a first coating composition comprising an antimicrobial polymer in a solvent. The polymer can be formed by mixing a plurality of monomers in a suitable solvent (e.g., an organic solvent such as isopropyl alcohol, for example) as disclosed herein. In some embodiments, a relatively small portion (e.g., 3%) of the solvent can comprises acidified water. Acidified water in the reaction mixture can facilitate bonding between silane groups in the composition and between silane groups in the composition and a substrate comprising active silanes. Optionally, after forming the antimicrobial polymer, the polymer composition can be diluted, as described above, before contacting it with a substrate.

The method may include optional step of mixing the first coating composition with a free second cationic compound and/or a free second organosilane compound. Suitable second cationic compounds are described in U.S. Pat. No. 6,504,583; and include antimicrobial silanated quaternary amine compounds such as N,N-dimethyl-N-(3-(trimethoxysilyl)propyl)-1-octadecanaminium chloride (CAS Number 27668-52-6), for example. Suitable second organosilane compounds comprise hydrolyzable groups and can facilitate the formation of crosslinks between silanated compounds and/or crosslinks between silanated compounds and a siliceous substrate. Examples of suitable second organosilane compounds include alkyl halide organosilane compounds and trimethoxysilyl compounds (e.g., 3-chloropropyltrimethoxysilane).

The method further comprises providing a first substrate with a first surface and a second surface. Typically, the first surface is a patient-contact surface, as described herein.

The method further comprises the step of contacting the first coating composition with the first surface of the first substrate under conditions suitable to facilitate adherence between the antimicrobial polymer and the first surface. Initially, the first coating composition, which may optionally include a free antimicrobial organosilane, is applied to the first surface of the first substrate. The first substrate may be any of the suitable substrates disclosed herein. In some embodiments, the first surface of the first substrate may comprise a coating (e.g., a siliceous coating on a substrate such as a polymer or glass substrate, for example). In some embodiments, the first substrate may be glass, a polymer film, or a diamond-like glass material. Suitable diamond-like glass materials are described in U.S. Pat. Nos. 6,696,157; 6,015,597; and 6,795,636; and U.S. Patent Publication No. US 2008/196664, each of which is incorporated herein by reference in its entirety.

The first coating composition may be applied to the substrate by a variety of processes known in the art such as, for example, wiping, brushing, dip coating, curtain coating, gravure coating, kiss coating, spin coating, and spraying.

Contacting the first coating composition with the substrate further comprises contacting the composition under conditions that facilitate adherence of the antimicrobial polymer and/or the free cationic organosilane, if present , to the first surface of the first substrate. A person having ordinary skill in the art will appreciate that during and after the period which solvent in which the first coating composition is dissolved and/or suspended evaporates, components of the first coating composition will begin reacting with each other and, optionally, with active silane groups on the first surface of the first substrate to form Si—O—Si bonds. This reaction will proceed relatively slowly at ambient temperature (circa 23° C.). Heating the first substrate can facilitate the formation of cross-linking covalent bonds between the silane groups in the antimicrobial polymer composition and the silane groups, if present, on the first surface of the substrate. Thus, in certain embodiments, the formation of the Si—O—Si bonds can be accelerated by the optional step of exposing the coated first substrate to an elevated temperature. Without being bound by theory, other forces (e.g., hydrophobic interaction, electrostatic interaction, hydrogen bonding, adhesion) also may facilitate adherence of components of the antimicrobial coating composition to the first surface of the first substrate.

In general, exposing the first substrate to higher temperatures while contacting it with the polymer composition will require shorter times for the solvent to evaporate and for the polymer to adhere to the first substrate. However, the contacting step should be performed at temperatures below which siloxane bonds dissociate. For example, in some embodiments, the contacting step can be conducted at about ambient temperature (20-25° C.) for about 10 minutes to about 24 hours. In some embodiments, the contacting step can be conducted at about 130° C. for about 30 seconds to about 3 minutes. The conditions for the contacting step can have a significant impact on the properties of the polymer coating on the substrate. For example, a polymer contacted ("cured") at room temperature for 24 hours can be measurably more hydrophobic than a polymer cured at about 130° C. for about 3 minutes. In some embodiments, the hydrophobicity of the coating correlates with the durability of the polymer coating on the first surface of the first substrate.

In some embodiments (not shown), the method optionally includes pre-treatments of the first surface of the substrate by priming, plasma etching, corona for interfacial adhesion of the coating to surface.

In some embodiments , the method optionally includes post treatments of the coating by heating or irradiations including UV, IR plasma, E-beam for further improvent of interfacial adhesion of the coating to first surface of the substrate. These treatments can promote inter-polymer crosslinking, as well as promote covalent linkages between the polymer and the first surface, thereby improving the durabililty of the coating on the first surface of the substrate. If the first substrate is exposed to an elevated temperature, the method may include cooling the substrate. Typically, the substrate is cooled to room temperature.

In some embodiments, the method optionally includes the step of coupling the first substrate to a second substrate. The first substrate may be coupled to the second substrate before or after the step of contacting the first coating composition or first mixture with the first substrate. The second substrate may be any suitable substrate described herein. For example, the second substrate may be a polymer layer and the first substrate may be a glass or diamond-like coating and the polymer may be applied to the first substrate after the first substrate is coated onto the second substrate. In an alternative embodiment, the first substrate may be a polymer film with adhesive on one major surface of the film. In the alternative embodiment, the polymer composition may be applied to the major surface of the film opposite the adhesive and the polymer-coated adhesive film may subsequently be coupled via the adhesive to a second substrate such as a glass or polymer layer, for example.

In some embodiments, the method further comprises a step of applying a layer to the first substrate. The first substrate may be any suitable substrate described herein to which a layer may be applied. The layer can comprise a metal oxide (e.g., an oxide of silica, zirconium, aluminum, tin, antimony, or mixtures or a combination of any two or more of the foregoing metal oxides). The layer may be applied by methods that are known to a person of ordinary skill in the art. A nonlimiting example of applying a siliceous layer to a substrate is described in Example 1 of U.S. Pat. No. 7,294,405; wherein an antiglare hard coat siliceous layer is applied to a glass substrate. In these embodiments, the method further includes forming a first coating composition comprising the vinyl polymer in a solvent, as described above, for example. Optionally, the these embodiments may include the step of adding to the first coating composition a second cationic compound. The method further includes contacting the first coating composition to the coated layer. The first coating composition can be applied by any suitable coating method, such as the coating methods described herein, for example. Contacting the first coating composition with the coated layer further comprises contacting the first coating composition with the coated layer under conditions suitable to facilitate the adherence of the composition to the coated layer (e.g., using conditions described herein to adhere the vinyl polymer to the first substrate). Optionally, contacting the first coating composition with the first substrate may further comprise treating the vinyl polymer-coated substrate with actinic and/or ionizing radiation (e.g., ultraviolet light, e-beam, plasma, or the like). This treatment can promote inter-polymer crosslinking, as well as promote covalent linkages between the polymer and the substrate, thereby improving the durabililty of the coating on the surface of the substrate.

It should be noted that, in any embodiment of the methods disclosed herein, pretreatment of the substrate prior to applying antimicrobial polymer compositions of the present disclosure can improve the bonding between the polymer and the substrate (e.g., siliceous material). Pretreatment of the the substrate may include, for example, soaking the substrate in a volatile solvent (e.g., water, isopropyl alcohol) and/or wiping the substrate with the volatile solvent. Optionally, the solvent may further comprise a composition of a basic compound such as potassium hydroxide, for example. In some embodiments, the solvent may be saturated with the composition of the basic compound.

In particular, pretreatments that include heating the substrate from about 30 degrees C. to about 200 degrees C. (preferably, about 30 degrees C. to about 150 degrees C.) for 20 minutes to 60 minutes can improve the bonding between the polymer and the substrate.

In some embodiments, pretreatment by heating the substrate shortly before the antimicrobial coating is applied results in improved bonding (e.g., as measured by the durability of the coating) between the coating and the substrate. The improved bonding can result in significantly greater durability of the polymer layer on the substrate. Without being bound by theory, it is believed that pretreatment of the substrate by heating removes excess moisture and other impurities (e.g., organic residues) present on the surface of the substrate (e.g., siliceous material) and provides greater ability of the surface silane groups to react with the silanated polymers and/or compounds in the coating compositions disclosed herein.

Antimicrobial Leaching Test Procedure for Coated Articles:

Antimicrobial polymer coatings of the present disclosure are durable (i.e., substantially non-leachable). The following method can be used to test the release of diffusible antimicrobial activity from polymer-coated articles of the present disclosure.

The non-leaching nature of the antimicrobial polymer on a surface can be demonstrated using zone of inhibition testing according to Section 12 of ASTM E2149-01 entitled "Standard Test Method for Determining the Antimicrobial Activity of Immobilized Antimicrobial Agents Under Dynamic Contact Conditions". The zone of inhibition is presented as a distance in millimeters from the source of an antimicrobial agent in which the antimicrobial is effective. Preferably, the zone is ≤3 mm; more preferably, the zone is ≤1 mm; even more preferably, the zone is 0 mm.

EMBODIMENTS

Embodiment A is an article, comprising:
 a coating composition comprising a vinyl polymer having a plurality of pendant groups comprising
  a first pendant group comprising a cationic component;
  a second pendant group comprising a nonpolar component;
  a third pendant group comprising a first organosilicon component; and
 a medical device comprising an elastomeric first substrate having a patient-contact first surface and a second surface;
  wherein the vinyl polymer is durably adhered to the patient-contact first surface, and
  wherein the composition is essentially free of inorganic filler.

Embodiment B is the article of embodiment 1, wherein the cationic component is selected from the group consisting of a quaternary amine component, protonated tertiary amine component, and a protonated secondary amine component.

Embodiment C is the article of any one of the preceding embodiments, wherein the organosilicon component comprises an organosilane or an organic silane ester.

Embodiment D is the article of any one of the preceding embodiments, wherein the coating composition was deposited and cured with an additional free silane present in the coating composition.

Embodiment E is the article of embodiment D, wherein the additional free silane is a quarternary ammonium silane or protonated tertiary amino silane having at least one straight or branched chain alkyl of 6-22 carbon atoms.

Embodiment F is the article of any one of the preceding embodiments, wherein the composition further comprises an adhesion-promoting component.

Embodiment G is the article of any one of the preceding embodiments, wherein the polymer does not comprise a pendant group that includes a carboxylate or alkoxylate chemical group.

Embodiment H is the article of any one of the preceding embodiments wherein, in the vinyl polymer, the ratio of cationic amine molar equivalents to organosilicon molar equivalents is about 0.1:1 to about 10:1.

Embodiment I is the article of any one of the preceding embodiments, wherein the total nonleachable cationic amine concentration derived from cationic groups on the polymer and any cationic quaternary amino, protonated tertiary amino, or protonated secondary amino silane present is at least 300 grams nonvolatile coating composition/equivalent cationic group and not more than 3000 grams nonvolatile coating composition/equivalent cationic group.

Embodiment J is the article of any one of the preceding embodiments, wherein the silane equivalent weight of the coating composition derived from silane functionality on the polymer and on any free silane present in the coating composition is at least 200 grams of nonvolatile coating composition/equivalent silane and not more than 4000 grams nonvolatile coating composition/equivalent silane group.

Embodiment K is the article of any one of the preceding embodiments, wherein at least one of the pendant components comprises a fluorochemical.

Embodiment L is the article of of embodiment K, wherein the second pendant group comprises a fluorochemical.

Embodiment M is the article of any one of the preceding embodiments, wherein the patient-contact surface to which the vinyl polymer is adhered is a glass, metal, metal oxide, ceramic, or polymeric surface.

Embodiment N is the article of of embodiment M, wherein the polymeric surface comprises a flexible polymeric surface.

Embodiment O is the article of any one of the preceding embodiments, wherein the first substrate further comprises a durable metal oxide layer on the first surface.

Embodiment P is the article of embodiment O, wherein the metal oxide layer comprises an oxide of silicon, zirconium, aluminum, or a combination of any two or more of the foregoing metal oxides; wherein the vinyl polymer is adhered to the metal oxide layer.

Embodiment Q is the article of any one of the preceding embodiments, wherein the second side of the first substrate is adhered to a second substrate.

Embodiment R is the article of embodiment Q, wherein the first substrate is adhered to the second substrate by a chemical bond, a thermal bond, an adhesive, a mechanical fastener, or a combination of any of the foregoing.

Embodiment S is the article of any one of the preceding embodiments, wherein the medical device comprises an endoscope, an endotracheal tube, an intravascular catheter, a urinary catheter, a wound dressing, a stethoscope diaphragm, stethoscope tubing, stethoscope chest piece, ventilator tubing, patient feeding tubes, surgical drains, and other flat, tubular or shaped flexible medical devices intended for contact with mammalian tissue.

Embodiment T is an article, comprising:
a coating composition comprising a vinyl polymer having a plurality of pendant groups comprising
  a first pendant group comprising a cationic component;
  a second pendant group comprising a nonpolar component;
  a third pendant group comprising a first organosilicon component; and
an elastomeric body fluid-contacting substrate having a body fluid-contacting first surface and a second surface;
  wherein the vinyl polymer is durably adhered to the body fluid-contacting first surface, and
  wherein the composition is essentially free of inorganic filler.

Embodiment U is the article of embodiment T, wherein the cationic component is selected from the group consisting of a quaternary amine component, protonated tertiary amine component, and a protonated secondary amine component.

Embodiment V is the article of embodiment T or embodiment U, wherein the organosilicon component comprises an organosilane or an organic silane ester.

Embodiment W is the article of any one of embodiments T through V, wherein the coating was deposited and cured with an additional free silane present in the composition.

Embodiment X is the article of embodiment W, wherein the additional free silane is a quarternary ammonium silane or protonated tertiary amino silane having at least one straight or branched chain alkyl of 6-22 carbon atoms.

Embodiment Y is the article of any one embodiments T through X, wherein the composition further comprises an adhesion-promoting component.

Embodiment Z is the article of any one of embodiments T through Y, wherein the polymer does not comprise a pendant group that includes a carboxylate or alkoxylate chemical group.

Embodiment AA is the article of any one of embodiments T through Z wherein, in the vinyl polymer, the ratio of cationic amine molar equivalents to organosilicon molar equivalents is about 0.1:1 to about 10:1.

Embodiment BB is the article of any one of embodiments T through AA, wherein the total nonleachable cationic amine concentration derived from cationic groups on the polymer and any cationic quaternary amino, protonated tertiary amino, or protonated secondary amino silane present is at least 300 grams nonvolatile coating composition/ equivalent cationic group and not more than 3000 grams nonvolatile coating composition/equivalent cationic group.

Embodiment CC is the article of any one of embodiments T through BB, wherein the silane equivalent weight of the coating composition derived from silane functionality on the polymer and on any free silane present in the coating composition is at least 200 grams of nonvolatile coating composition/equivalent silane and not more than 4000 grams nonvolatile coating composition/equivalent silane group.

Embodiment DD is the article of any one of embodiments T through CC, wherein at least one of the pendant components comprises a fluorochemical.

Embodiment EE is the article of embodiment DD, wherein the second pendant group comprises a fluorochemical.

Embodiment FF is the article of any one of embodiments T through EE, wherein the patient-contact surface to which the vinyl polymer is adhered is a glass, metal, metal oxide, ceramic, or polymeric surface.

Embodiment GG is the article of embodiment FF, wherein the polymeric surface comprises a flexible polymeric surface.

Embodiment HH is the article of any one of embodiments T through GG, wherein the first substrate further comprises a durable metal oxide layer on the first surface.

Embodiment II is the article of embodiment HH, wherein the metal oxide layer comprises an oxide of silicon, zirconium, aluminum, or a combination of any two or more of the foregoing metal oxides; wherein the vinyl polymer is adhered to the metal oxide layer.

Embodiment JJ is the article of any one of embodiments T through II, wherein the second side of the first substrate is adhered to a second substrate.

Embodiment KK is the article of embodiment JJ, wherein the first substrate is adhered to the second substrate by a chemical bond, a thermal bond, an adhesive, a mechanical fastener, or a combination of any of the foregoing.

Embodiment LL is a method of making a coated article, the method comprising:

forming a first coating composition comprising a vinyl polymer having a plurality of pendant groups comprising
- a first pendant group comprising a first cationic component;
- a second pendant group comprising a nonpolar component;
- a third pendant group comprising a first organosilicon component;
- wherein the first coating composition is essentially free of inorganic filler; and
- contacting the first coating composition with a first surface of a first substrate under conditions suitable to adhere the polymer to the first surface;
- wherein the first substrate comprises an elastomeric component of a medical device.

Embodiment MM is the method of embodiment LL, wherein forming a coating first coating composition comprises forming a first coating composition comprising an adhesion-promoting component.

Embodiment NN is the method of embodiment LL or embodiment MM, wherein forming a first coating composition comprises forming an emulsion or a dispersion of the vinyl polymer in a solvent.

Embodiment OO is the article method of any one of embodiments LL through NN, wherein forming the first coating composition further comprises forming a first coating composition comprising a catalyst compound to accelerate the silane hydrolysis and/or condensation reactions during cure.

Embodiment PP is the method of any one of embodiments LL through OO, wherein forming the first coating composition further comprises forming a first coating composition comprising an adhesion promoter.

Embodiment QQ is the method of any one of embodiments LL through PP, wherein forming a first coating composition further comprises forming a first coating composition comprising a free second cationic silane component and/or a second cationic component.

Embodiment RR is the method of any one of embodiments LL though QQ, further comprising, after contacting the first coating composition with the surface, immersing and/or rinsing the surface.

Embodiment SS is the method of any one of embodiments LL through RR, further comprising coupling the first substrate to a second substrate.

Embodiment TT is the method of any one of embodiments LL through SS, further comprising contacting a second coating composition with the first surface of the first substrate prior to contacting the first coating composition with the first surface of the first substrate.

Embodiment UU is a method of making a coated article, the method comprising: forming a first coating composition comprising a vinyl polymer having a plurality of pendant groups comprising
- a first pendant group comprising a first cationic component;
- a second pendant group comprising a nonpolar component;
- a third pendant group comprising a first organosilicon component;
- wherein the first coating composition is essentially free of inorganic filler; and
- contacting the first coating composition with a first surface of a first substrate under conditions suitable to adhere the polymer to the first surface;
- wherein the first substrate comprises an elastomeric body fluid-contacting substrate.

Embodiment VV is the method of embodiment UU, wherein forming a first coating composition comprises forming a first coating composition comprising an adhesion-promoting component.

Embodiment WW is the method of embodiment UU or embodiment VV, wherein forming a first coating composition comprises forming an emulsion or a dispersion of the vinyl polymer in a solvent.

Embodiment XX is the method of any one of embodiments UU through WW, wherein forming the first coating composition further comprises forming a first coating composition comprising a catalyst compound.

Embodiment YY is the method of any one of embodiments UU through XX, wherein forming the first coating composition further comprises forming a first coating composition comprising an adhesion promoter.

Embodiment ZZ is the method of any one of embodiments UU through YY, wherein forming a first coating composition further comprises forming a first coating composition comprising a free second cationic silane component and/or a second cationic component.

Embodiment AAA is the method of any one of embodiments UU though ZZ, further comprising, after contacting the first coating composition with the surface, immersing and/or rinsing the surface.

Embodiment BBB is the method of any one of embodiments UU through AAA, further comprising coupling the first substrate to a second substrate.

Embodiment CCC is the method of any one of embodiments UU through BBB, further comprising contacting a second coating composition with the first surface of the first substrate prior to contacting the first coating composition with the first surface of the first substrate.

Embodiment DDD an article made according to the method of any one of embodiments UU through CCC.

Embodiment EEE is a medical device article comprising a coating wherein the coating is derived from:
a composition comprising a free silane component and a vinyl polymer having a plurality of pendant groups comprising
- a first pendant group comprising a first quaternary ammonium component;
- a second pendant group comprising a first organosilicon component;
- wherein the vinyl polymer is durably adhered to the surface.

Embodiment FFF is the medical device article of embodiment EEE, wherein the composition is essentially free of inorganic filler.

Embodiment GGG is the medical device article of embodiment EEE or embodiment FFF, wherein the free silane is a quaternary ammonium silane.

Embodiment HHH is the medical device article of embodiment GGG, wherein the free quaternary ammonium silane comprises at least one linear or branched C8-C22 alkyl group attached to the quaternary amine The invention will be further illustrated by reference to the following non-limiting Examples. All parts and percentages are expressed as parts by weight unless otherwise indicated.

EXAMPLES

The present invention is more particularly described in the following examples that are intended as illustrations only, since numerous modifications and variations within the scope of the present invention will be apparent to those skilled in the art. Unless otherwise noted, all parts, percentages, and ratios reported in the following examples are on a weight basis, and all reagents used in the examples were obtained, or are available, from the chemical suppliers described below, or may be synthesized by conventional techniques.

A list of reagents used in the following examples in shown in Table 1.

TABLE 1

| Abbreviation | Chemical Name | Source |
|---|---|---|
| A1120 | NH2—(CH2)2NH—(CH2)3Si(OCH3)3 (Silane adhesion promoter) | Union Carbide, Houston, TX |
| A-174 | Methacryloylpropyl trimethoxy silane | Aldrich; Milwaukee, WI |
| Silane 1 | 3-(trimethoxysilyl)-propyldimethyloctadecyl ammonium chloride 50% in methanol (CAS# 27668-52-6) | Petrarch Systems Inc. Bristol, PA 19007 |
| Silane 2 | SiO6620.0, lot 9H-7773, Octadecyl dimethyl (3-(trimethyl silyl)-propyl) ammonium chloride 60% in methanol (CAS# 27668-52-6) | Gelest Inc, Tullyform, PA |
| Silane 3 | Octadecyl dimethyl (3-(trimethyl silyl)-propyl) ammonium chloride , 42% in methanol. (CAS# 27668-52-6) | Aldrich; Milwaukee, WI |
| BHT | 2,6-Di-tert-4-methyl phenol | Aldrich; Milwaukee, WI |
| $C_{16}H_{33}Br$ | 1-bromohexadecane | Chemtura Corporation, Bay Minette, AL |
| DBU | 1,8-diazabicyclo-5,4,0-undec-7-ene | Aldrich; Milwaukee, WI |
| DMAEMA | Dimethylaminoethyl methacrylate | CIBA; Marietta, GA |
| DMAEMA-C16Br | Dimethylaminoethyl methacrylate C16 bromide | See Example 1 |
| EtOAc | Ethyl acetate | J.T. Baker; Austin, TX |
| EtOH | Ethanol | J.T. Baker; Austin, TX |
| IOA | Iso-octyl acrylate | Sartomer USA, LLC; Exton, PA |
| IPA | Isopropyl alcohol | VWR; Houston, TX |
| MEHQ | 4-Methoxyphenol | Alfa Aesar, Ward Hill, MA |
| Sn(Oct)$_2$ | Stannous octoate | Alfa Aesar, Ward Hill, MA |
| Vazo-67 | 2,2-Azobis (2-methylbutyronitrile) | Dupont; Wilmington, DE |

Silane 1, 2 and 3 are the same chemical (CAS# 27668-52-6) supplied by 3 different sources.

Synthesis of DMAEMA-$C_{16}$Br Monomer

In a clean reactor; fitted with an overhead condenser, mechanical stirrer, and a temperature probe; were charged 918 parts by weight of acetone, 807 parts of $C_{16}H_{33}Br$, 415.5 parts of DMAEMA, 2.0 parts of BHT and 2.0 parts of MEHQ. The batch was stirred at 150 rpm and a mixed gas (90/10 $O_2/N_2$) was purged through the solution throughout the reaction scheme. The mixture was heated to 74° C. for 18 hours. A sample was taken out for analysis by gas chromatography (GC) and which revealed the conversion of >98% of the reactants to the desired product. At this point 918 parts of EtOAc was added slowly with stirring at very high speed. A white solid started to precipitate out. The heating was stopped and the mixture was cooled to room temperature. The reaction precipitate was recovered by filtration and the white solid material was washed with 200 parts of cold EtOAc. The solid material was dried in a vacuum oven at 40° C. for 8 hours. The dried product was analyzed by nuclear magnetic resonance (NMR) spectroscopy, which revealed the presence of >99.9% pure DMAEMA-$C_{16}$Br monomer.

Synthesis of Antimicrobial Polymer (AMP)

In a clean reaction bottle, the monomers (e.g. 50 parts of DMAEMA-$C_{16}$Br monomer, 10 parts of A-174 monomer, and 40 parts of IOA monomer) were combined with 0.5 parts of Vazo-67 and 300 parts of IPA. The mixture was purged with dry nitrogen for 3 minutes. The reaction bottle was sealed and placed in a 65° C. preheated water bath with mixing. The reaction mixture was heated for 17 hours at 65° C. with mixing. The viscous reaction mixture was analyzed for % solids and found to be 25% solids in IPA. To drive the reaction of the residual monomer to >99.5% completion, an additional 0.1 parts of Vazo-67 was added to the mixture, the solution was purged and sealed. The bottle was placed in the 65° C. water bath with mixing and heated for 8 hours. A conversion of greater than 99.5% of the monomers was achieved, as evident by % solids calculation. The polymers in the Examples were made according to this process. The polymer designation (e.g., "p(DMAEMA-C16Br/A-174/IBMA)" refers to the combination of monomers used in the reaction mixture. The polymer has a cationic amine equivalent weight of 925.1 g polymer/equivalent cationic amine and a silane (organosilicon) equivalent weight of 2484 g polymer/equivalent Si (silane).

Example 1

Preparation of Antimicrobial Polymer-Coated Medical-Grade Elastomeric Material and Demonstration of Antimicrobial Activity (2-Hour Contact Time)

The purpose of Example 1 was to coat formulations on a silicone sheet to mimic a coating on a catheter or other elastomeric low surface energy medical device and assess the antimicrobial performance of those coatings. Coating formulations were prepared according to Table 2.

Silicone sheeting of Silastic ® Q7-4840 Biomedical grade silicone rubber kit, 0.02" thick (510 microns) NRV M/M 40D, 30.5 cm×30.5 cm (12 inch×12 inch) was obtained from Specialty Manufacturing, Inc., Saginaw, Mich. Rectangles of 12.7 cm×7.6 cm (5 inch×3 inch) size were cut out of this sheet and used as a coating substrate for the formulations shown in Table 2.

Sample-Coating Process:

500 µL of each of the formulations was pipetted onto 12.7 cm×7.6 cm (5 inch×3 inch) silicone sheet rectangles and spread out to evenly coat the surface. Samples were allowed to stand at room temperature for a period of 15 minutes. The excess solution was drained off. Samples were then dried in an oven for a period of 15 minutes at 120° C. Samples were then thoroughly rinsed in DI water and left out at room temperature overnight. Four circular punches of size 1.6 cm (⅝ inch) diameter were cut out from each of the samples and submitted for microbiological testing. Sample 7, the uncoated silicone sheet control, was washed in IPA, heated at 120° C. for 15 minutes and then thoroughly rinsed in DI water, left out at room temperature overnight, prior to microbiological testing.

Microbiological Testing—2 Hour Kill Time Test:

The JIS Z 2801 test method (Japan Industrial Standards; Japanese Standards Association; Tokyo, JP) was used to evaluate the antibacterial activity of antibacterial polymer-coated silicon substrates with minor modifications. An overnight (O/N) culture of Staphylococcus aureus ATCC 25923 was started in tryptic soy broth (TSB) and allowed to grow for 18-24 hours at 37° C. A 1:10 dilution of the O/N culture was made in phosphate buffered water (PBW). The 1.6 cm diameter circular cut outs of the coated silicone sheets were placed on sterile coverslips for support since the silicone sheets were thin. An amount of 100 µL of the diluted bacteria was placed onto the coating. The sample with the cover slip/silicone was placed into a sterile petri dish that went into a plastic storage bag with a wet paper towel and then the bac was placed into an incubator at 28° C. for two hours. At zero and two hours, the samples were placed into 20 mL of D/E (Dey-Engley) neutralizing broth, and sonicated for 2 minutes and vortexed for 1 minute for recovery of bacteria. Plating was carried out at time 0 and 2 hours. At time 0, one replicate per sample for all of the samples 1-7 was plated. At time 2 hours, 3 replicates per sample for all samples 1-7 were plated; from neat to −4 dilutions on 3M AEROBIC PETRIFILM. An amount of 5.63 logs of bacteria was used as an input control. The bacteria was neutralized and plated as described above to show maximum number of bacteria that can be recovered. Sample 7 was the no active control as it was the uncoated sample. Bacteria was recovered from this sample and matched the input control. In addition, every sample was neutralized for 5 minutes prior to adding bacteria for 0 minutes and then plated. These samples at "0 time" served also as a neutralization check as seen in ASTM1054 E1054-08 Standard Test Methods for Evaluation of Inactivators of Antimicrobial Agents. The samples showed values similar to the input control, which indicated that no kill was obtained at "0 time." For the 2 hour sample, bacteria were left in contact with the sample for a period of 2 hours followed by neutralization and plating as described above.

TABLE 2

EXAMPLE 1 (2 hour kill time)

| Sample No. | 1 | 2 | 3 | 4 | 5 | 6 | 7 |
|---|---|---|---|---|---|---|---|
| AMP % | 5.00 | 5.00 | 5.00 | 5.00 | 5.00 | — | — |
| Silane 1% | — | 2.13 | 2.00 | 2.00 | — | 2.00 | — |
| A1120 % | — | — | 1.20 | 1.10 | 1.20 | 1.20 | — |
| Sn(Oct)₂ % | — | — | 0.13 | 0.50 | 0.50 | 0.15 | — |
| IPA % | 95.0 | 92.87 | 91.67 | 91.40 | 93.3 | 98.65 | — |
| Log Red. | 0.71 | −0.11 | 5.26 | 5.16 | 2.69 | 5.05 | −0.13 |
| Std Dev | 0.11 | 0.05 | 0.57 | 0.40 | 0.50 | 0.54 | 0.03 |

AMP: p(DMAEMA-C16Br/IOA/A174) 50/40/10 −25% in isopropyl alcohol.

Sample 7 was an uncoated silicone sheet; a control.

For this example the calculated cationic and silane equivalent weights (eqwts) for the compositions are shown below:

Example 1

| Sample No. | 1 | 2 | 3 | 4 | 5 | 6 |
|---|---|---|---|---|---|---|
| Cationic eqwt | 925.1 | 662 | 668 | 668 | 925.1 | 668 |
| Silane eqwt | 2484 | 874 | 285 | 301 | 212 | 284 |
| Ratio equiv cation/equiv silane | 2.7 | 1.3 | 0.4 | 0.5 | 0.2 | 0.4 |

Example 2

Demonstration of Antimicrobial Activity of Coated Antimicrobial Polymer (15-Minute Contact Time)

The samples for Example 2 were prepared as described in TABLE 3, below. Silicone sheeting used in Example 1 was washed in hot water, rubbed with soap (VWR Softcide hand soap Cat # 56700-124)), rinsed in hot tap water, and finally rinsed in DI water. Pieces of 12.7 cm×10.2 cm (5 inch×4 inch) samples were cut out and 1000 µL of solution was spread out on the surface. Samples were allowed to stand for 15 minutes at room temperature then heated at 120° C. for 15 minutes to dry and finally left at room temperature overnight. Samples were rinsed in DI water, and then cut into 1.6 cm (⅝ inch) diameter circular punches for microbiological testing.

Microbiological Testing—15 Minute Kill Time Test:

The JIS Z 2801 test method (Japan Industrial Standards; Japanese Standards Association; Tokyo, JP) was used to evaluate the antibacterial activity of antibacterial polymer-coated silicon substrates with minor modifications. An overnight (O/N) culture of Staphylococcus aureus ATCC 25923 was started in tryptic soy broth (TSB) and allowed to grow for 18-24hours at 37° C. The 1.6 cm diameter circular cut outs of the coated silicone sheets were placed on sterile coverslips for support since the silicone sheets were thin. 100 µL of the diluted bacteria was placed onto the coating and the sample with the cover slip/silicone was placed on a sterile petri dish that went into a plastic storage bag with a wet paper towel and then the bag was placed into an incubator at 28° C. for 15 minutes. At zero and 15 minutes, the samples were placed into 20 mL of D/E neutralizing broth, and sonicated for 2 minutes and vortexed for 1 min for recovery of bacteria. Plating was carried out at time 0 and 15 minutes. At each time 2 replicates per sample for all of the samples 1-7 were plated from neat to −4 dilutions on 3M AEROBIC PETRIFILM. An amount of 5.31 logs of bacteria was used as an input control. The bacteria was neutralized and plated as described above to show maximum number of bacteria that can be recovered. Sample 8 was the no active control as it was the uncoated sample. Bacteria were recovered from this sample and matched the input control. The samples at "0 time" were obtained by adding bacteria to the sample and immediately neutralizing and plating the sample. The samples showed value similar to the input control, which indicated that no kill was obtained at "0 time". For the 15 minute sample, bacteria were left in contact with the sample for a period of 15 minutes followed by neutralization and plating as described above. Log reductions were calculated based on subtracting values at specific time points against the input control.

TABLE 3

EXAMPLE 2 (15 minute kill time)

| Sample No. | 1 | 2 | 3 | 4 | 5 | 6 | 7 | 8 |
|---|---|---|---|---|---|---|---|---|
| AMP % | 3.00 | — | 3.00 | 3.00 | 3.00 | — | 3.00 | — |
| Silane 2% | — | 3.00 | 3.00 | 3.00 | 3.00 | 3.00 | — | — |
| A1120 % | — | — | — | 1.05 | 1.10 | 1.05 | 1.10 | — |
| Sn(Oct)$_2$ % | — | — | — | 0.12 | 0.12* | 0.11 | 0.10 | — |
| IPA % | 97.0 | 97.0 | 94.0 | 92.84 | 92.4 | 95.84 | 95.8 | — |
| Log Red. | −0.05 | −0.07 | 0.00 | 2.68 | 2.33 | 1.25 | −0.02 | −0.02 |
| Std Dev | 0.02 | 0.06 | 0.02 | 0.29 | 0.16 | 0.09 | 0.03 | 0.08 |

Sample 8 was an uncoated silicone sheet; a control.
*For sample 5: 1,8-diazabicyclo-5,4,0-undec-7-ene (DBU) was used instead of Sn(Oct)$_2$ For this example the calculated cationic and silane eqwts for the compositions are shown below:

Example 2

| Sample No. | 1 | 2 | 3 | 4 | 5 | 6 | 7 |
|---|---|---|---|---|---|---|---|
| Cationic eqwt | 925.1 | 496.3 | 574.6 | 574.6 | 574.6 | 496.3 | 925.1 |
| Silane eqwt | 2484 | 496.3 | 649.1 | 294.8 | 287.3 | 215.6 | 142.9 |
| Ratio equiv cation/equiv silane | 2.7 | 1.0 | 1.1 | 0.5 | 0.5 | 0.4 | 0.2 |

Example 3

(15 Minute Kill Time Double Coated)

Silicone sheets as used in Example 1 were coated with the formulations described in Table 4, below, in a manner similar to Examples 1 and 2. However, in this experiment, 1000 μL of each formulation was added to a 12.7 cm×10.2 cm (5 inch×4 inch) silicone sheet for and left at room temperature for 15 minutes. Then, for each sample, a second dose of 1000 μL of the same formulation was added to the silicone sheet and again left at room temperature for 15 minutes. Samples were then dried at 120° C. for 10 minutes. The coating appeared to be uniform over the entire surface. Finally, the coated samples were then allowed to stand at room temperature overnight.

Observations were made for durability of the coatings before and after soaking the prepared samples in 99 mL of phosphate buffered water (Butterfield's Phosphate-Buffered Dilution Water) for 19 hours. Samples 4, 6, 7 and 8 were also evaluated for the ability to kill bacteria within 15 minutes before and after treatment with phosphate buffered water. The microbiological testing was done as described in Example 2. Duplicate samples were tested for the 15 minute time point. Log reductions were calculated based on subtraction against the input control.

Durability test of the AMP coating was performed by visually observing the coatings before and after PBW treatment. Samples were assigned a coating rating according to the following definitions.

| Coating Rating | Definition of Rating |
|---|---|
| 5 | Best; clear, shiny coating observed |
| 3 | Fair/Medium; some coating was observed but was discolored and/or cloudy and/or slightly dull |
| 1 | Worst; a dull looking surface indicating little or no coating at all |

TABLE 4

EXAMPLE 3 (15 minute kill time: double coated)

| Sample No. | 1 | 2 | 3 | 4 | 5 | 6 | 7 | 8 |
|---|---|---|---|---|---|---|---|---|
| AMP % | 3.00 | — | 3.00 | 3.00 | 3.00 | — | 3.00 | — |
| Silane #3% | — | 3.00 | 3.00 | 3.00 | 3.00 | 3.00 | — | — |
| A1120 % | — | — | — | 1.05 | 1.10 | 1.05 | 1.10 | — |
| Sn(Oct)$_2$ % | — | — | — | 0.12 | 0.12* | 0.11 | 0.10 | — |
| IPA % | 97.0 | 97.0 | 94.0 | 92.84 | 92.4 | 95.84 | 95.8 | — |
| Coating Before 15 min | 5 | 1 | 3 | 5 | 5 | 3 | 5 | 1 |
| Coating After 15 min | 5 | 1 | 3 | 5 | 5 | 3 | 5 | 1 |
| Ave Log Red. Before | — | — | — | 1.51 | — | 1.27 | 1.79 | −0.02 |
| Std Dev Before | — | — | — | 0.16 | — | 0.37 | 0.26 | 0.03 |
| Ave Log Red. After | — | — | — | 1.42 | — | 0.06 | −0.10 | −0.04 |
| Std Dev After | — | — | — | 0.52 | — | 0.05 | 0.04 | 0-07 |

Sample 8 was an uncoated silicone sheet; a control.
*For Sample 5: 1,8-diazabicyclo-5,4,0-undec-7-ene (DBU) was used instead of Sn(Oct)$_2$ Coating Flexibility Testing:

Samples 1-7 of EXAMPLE 3 were tested for the flexibility of the coating on the silicone sheet substrate surface. One replicate each of the 12.7 cm×10.2 cm (5 inch×4 inch) silicone sheet coated with the formulations of samples 1-7 were manually flexed by bending the sheet along a central axis, folding the sheet in half so that the opposite edges touched, a 180° bend of one edge to the opposite edge. Each sheet was then reverse folded 360° in the opposite direction. This 360° flex test was performed five times for one replicate of each of samples 1-7 of EXAMPLE 3. All samples 1-7 maintained their coating integrity; there was no cracking, flaking or signs of stress to any the coatings for these samples. Note that sample 2 had very little if any coating.

Example 4

LITTMANN Stethoscope diaphragm samples (part number 78-8078-2797-3, for LITTMANN Classic II SE and Cardiology III stethoscopes, available from 3M Company of St. Paul, Minn.) were washed in hot water and then in DI water. Samples were coated with 500 µL of each of the formulations described in the Table 5 and then allowed to stand at room temperature for 15 minutes. Samples were heated to 120° C. for 10 minutes and then left at room temperature overnight. Samples were washed in DI water, cut into ⅝ inch circular pieces and submitted for microbiological testing.

Microbiological testing was performed the same as in Example 2. There were 2 replicates/sample for time points 15 minutes and 2 hours. Log reductions were calculated based on subtracting values at specific time points against input control. The Input control was 5.48 Log average with 0.07 standard deviation. The working stock was 7.06 Log average with 1.44 standard deviation.

Observations were made for durability of the coatings of Example 4, as was done in Example 3: before and after soaking the prepared samples in 99 mL of phosphate buffered water (Butterfield's Phosphate-Buffered Dilution Water) for 21 hours.

TABLE 5

| Sample # | 1 | 2 | 3 | 4 | 5 | 6 | 7 | 8 |
|---|---|---|---|---|---|---|---|---|
| AMP % | 3.00 | — | 3.00 | 3.00 | 3.00 | — | 3.00 | — |
| Silane #3 % | — | 3.00 | 3.00 | 3.00 | 3.00 | 3.00 | — | — |
| A1120 % | — | — | — | 1.05 | 1.10 | 1.05 | 1.10 | — |
| Sn(Oct)$_2$ % | — | — | — | 0.12 | 0.12* | 0.11 | 0.10 | — |
| IPA % | 97.0 | 97.0 | 94.0 | 92.84 | 92.4 | 95.84 | 95.8 | — |
| Log Red. @ 15 min | 0.29 | 0.37 | 0.74 | 2.03 | 2.42 | 0.51 | 0.37 | 0.02 |
| Std Dev @ 15 min | 0.07 | 0.17 | 0.12 | 0.07 | 0.34 | 0.06 | 0.35 | 0.07 |
| Log Red. @ 2 hrs | 4.96 | 2.87 | 3.24 | 5.48 | 5.48 | 5.33 | −0.1 | −0.01 |
| Std Dev @ 2 hrs | 0.60 | 0.40 | 0.42 | 0.00 | 0.00 | 0.30 | 0.05 | 0.10 |
| Coating Before | 5 | 5 | 5 | 5 | 5 | 3 | 5 | 1 |
| Coating After | 5 | 1 | 3 | 5 | 5 | 3 | 5 | 1 |

Sample 8 was an uncoated stethoscope diaphragm; a control.
*For sample 5 used 1,8-diazabicyclo-5,4,0-undec-7-ene (DBU), instead of Sn(Oct)$_2$ Coating Flexibility Testing:

Samples 1-7 of EXAMPLE 4 were tested for the flexibility of the coating on the LITTMANN stethoscope diaphragm (epoxy) surface. After soaking the prepared samples in 99 mL of PBW for 21 hours, one replicate of diaphragm material coated with the formulations of samples 1-7 of EXAMPLE 4 were manually flexed by bending the diaphragm material along a central axis, folding the sheet so that the opposite edges bended to form a 90° angle. Each sample was then folded 180° in the opposite direction. This 180° flex test was performed five times for each of samples 1-7 of EXAMPLE 4. The coated diaphragm samples of EXAMPLE 4 could not be flexed 360° as was done with EXAMPLE 3, because the diaphragm material substrate of the samples is made of a stiffer material than the silicone sheeting of EXAMPLE 3. All samples 1-7 of EXAMPLE 4 maintained their coating integrity; there was no cracking, flaking or signs of stress to any the coatings for these samples. Note that sample 2 had very little if any coating.

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

What is claimed is:

1. An article comprising:
a coating composition comprising a vinyl polymer having a plurality of pendant groups comprising
a first pendant group comprising a cationic component selected from the group consisting of a quaternary amine component, protonated tertiary amine component, and a protonated secondary amine component;
a second pendant group comprising a nonpolar component wherein the second pendant group is selected from the group consisting of linear or branched alkanes, alkaryl, aralkyl, aromatic groups, and combinations thereof; and a third pendant group
a third pendant group comprising a first organosilicon component;
wherein the vinyl polymer does not comprise a pendant group that comprises a carboxylate group; and
a medical device comprising an elastomeric first substrate having a patient-contact first surface and a second surface;
wherein the vinyl polymer is durably adhered to the patient-contact first surface, wherein the composition is free of inorganic filler; and
wherein the coating composition was deposited and cured with an additional free silane present in the coating composition; wherein the additional free silane is a quaternary ammonium silane or protonated tertiary amino silane having at least one straight or branched chain alkyl of 6-22 carbon atoms.

2. The article of claim 1, wherein the composition further comprises an adhesion-promoting component.

3. The article of claim 1, wherein the vinyl polymer does not comprise a pendant group that includes an alkoxylate chemical group.

4. The article of claim 1 wherein, in the vinyl polymer, the ratio of cationic amine molar equivalents to organosilicon molar equivalents is about 0.1:1 to about 10:1.

5. The article of claim 1, wherein at least one of the pendant groups comprises a fluorochemical.

6. The article of claim 1, wherein the first substrate further comprises a durable metal oxide layer on the first surface, wherein the metal oxide layer comprises an oxide of silicon, zirconium, aluminum, or a combination of any two or more of the foregoing metal oxides; wherein the vinyl polymer is adhered to the metal oxide layer.

7. The article of claim 1, wherein the second surface of the first substrate is adhered to a second substrate.

8. An article comprising:
a coating composition comprising a vinyl polymer having a plurality of pendant groups comprising
a first pendant group comprising a cationic component selected from the group consisting of a quaternary amine component, protonated tertiary amine component, and a protonated secondary amine component;

a second pendant group comprising a nonpolar component wherein the second pendant group is selected from the group consisting of linear or branched alkanes, alkaryl, aralkyl, aromatic groups, and combinations thereof; and a third pendant group comprising a first organosilicon component;

wherein the vinyl polymer does not comprise a pendant group that comprises a carboxylate group; and an elastomeric body fluid-contacting first substrate having a body fluid-contacting first surface and a second surface;

wherein the vinyl polymer is durably adhered to the body fluid-contacting first surface, and wherein the composition is free of inorganic filler.

9. The article of claim 8, wherein the coating was deposited and cured with an additional free antimicrobial silane component present in the composition.

10. The article of claim 8, wherein the composition further comprises an adhesion-promoting component.

11. The article of claim 8, wherein the vinyl polymer does not comprise a pendant group that includes an alkoxylate chemical group.

12. The article of claim 8 wherein, in the vinyl polymer, the ratio of cationic amine molar equivalents to organosilicon molar equivalents is about 0.1:1 to about 10:1.

13. The article of claim 8, wherein at least one of the pendant groups comprises a fluorochemical.

14. The article of claim 8, wherein the first substrate further comprises a durable metal oxide layer on the first surface, wherein the metal oxide layer comprises an oxide of silicon, zirconium, aluminum, or a combination of any two or more of the foregoing metal oxides; wherein the vinyl polymer is adhered to the metal oxide layer.

15. A method of making a coated article, the method comprising:

forming a first coating composition comprising a vinyl polymer having a plurality of pendant groups comprising a first pendant group comprising a first cationic component selected from the group consisting of a quaternary amine component, protonated tertiary amine component, and a protonated secondary amine component;

a second pendant group comprising a nonpolar component wherein the second pendant group is selected from the group consisting of linear or branched alkanes, alkaryl, aralkyl, aromatic groups, and combinations thereof; and a third pendant group comprising a first organosilicon component;

wherein the vinyl polymer does not comprise a pendant group that comprises a carboxylate group; and wherein the first coating composition is free of inorganic filler; and contacting the first coating composition with a first surface of a first substrate to adhere the vinyl polymer to the first surface;

wherein the first substrate comprises an elastomeric component of a medical device or an elastomeric body fluid-contacting substrate.

16. A medical device article comprising a coating wherein the coating is derived from:

a composition comprising a free silane component and a vinyl polymer having a plurality of pendant groups comprising a first pendant group comprising a first quaternary ammonium component;

a second pendant group comprising a nonpolar component wherein the second pendant group is selected from the group consisting of linear or branched alkanes, alkaryl, aralkyl, aromatic groups, and combinations thereof; and a third pendant group comprising a first organosilicon component;

wherein the vinyl polymer does not comprise a pendant group that comprises a carboxylate group;

wherein the vinyl polymer is durably adhered to a surface of the article; and wherein the composition is free of inorganic filler.

17. The article of claim 1, wherein the second pendant group comprising the nonpolar component renders the vinyl polymer more hydrophobic than a polymer without the nonpolar component.

18. The article of claim 1, wherein the vinyl polymer is water insoluble.

* * * * *